United States Patent
Evans et al.

(10) Patent No.: US 11,572,408 B2
(45) Date of Patent: Feb. 7, 2023

(54) TREATMENT OF CANCER WITH A SEMAPHORIN-4D ANTIBODY IN COMBINATION WITH AN EPIGENETIC MODULATING AGENT

(71) Applicant: Vaccinex, Inc., Rochester, NY (US)

(72) Inventors: Elizabeth Evans, Bloomfield, NY (US); Ernest Smith, West Henrietta, NY (US); Maurice Zauderer, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 38 days.

(21) Appl. No.: 16/496,286

(22) PCT Filed: Mar. 14, 2018

(86) PCT No.: PCT/US2018/022414
§ 371 (c)(1),
(2) Date: Sep. 20, 2019

(87) PCT Pub. No.: WO2018/175179
PCT Pub. Date: Sep. 27, 2018

(65) Prior Publication Data
US 2021/0179708 A1  Jun. 17, 2021

Related U.S. Application Data

(60) Provisional application No. 62/473,731, filed on Mar. 20, 2017.

(51) Int. Cl.
| | | |
|---|---|---|
| *C07K 16/28* | (2006.01) | |
| *A61P 35/00* | (2006.01) | |
| *A61K 31/4406* | (2006.01) | |
| *A61K 31/706* | (2006.01) | |
| *A61K 39/395* | (2006.01) | |
| *A61K 39/00* | (2006.01) | |

(52) U.S. Cl.
CPC ...... *C07K 16/2803* (2013.01); *A61K 31/4406* (2013.01); *A61K 31/706* (2013.01); *A61K 39/3955* (2013.01); *A61P 35/00* (2018.01); *A61K 2039/505* (2013.01); *C07K 2317/76* (2013.01)

(58) Field of Classification Search
CPC ............ C07K 16/2803; C07K 2317/76; C07K 2317/73; C07K 16/28; A61K 31/4406; A61K 31/706; A61K 39/3955; A61K 2039/505; A61K 31/7068; A61K 45/06; A61K 39/39541; A61K 39/395; A61K 2300/00; A61P 35/00
See application file for complete search history.

(56) References Cited

U.S. PATENT DOCUMENTS

| | | | |
|---|---|---|---|
| 4,683,195 | A | 7/1987 | Mullis et al. |
| 4,873,192 | A | 10/1989 | Kunkel |
| 5,585,089 | A | 12/1996 | Queen et al. |
| 5,693,761 | A | 12/1997 | Queen et al. |
| 5,693,762 | A | 12/1997 | Queen et al. |
| 5,939,598 | A | 8/1999 | Kucherlapati et al. |
| 6,180,370 | B1 | 1/2001 | Queen et al. |
| 6,737,056 | B1 | 5/2004 | Presta |
| 9,249,227 | B2 | 2/2016 | Smith et al. |
| 2004/0132101 | A1 | 7/2004 | Lazar et al. |
| 2006/0023379 | A1 | 2/2006 | Chen et al. |
| 2006/0233793 | A1 | 10/2006 | Belin et al. |
| 2008/0219971 | A1* | 9/2008 | Smith ............... C07K 16/2803 424/130.1 |
| 2010/0285036 | A1 | 11/2010 | Smith et al. |
| 2010/0286036 | A1* | 11/2010 | Tamiz .................... C07K 14/28 514/5.9 |
| 2014/0072578 | A1 | 3/2014 | Smith et al. |
| 2016/0115240 | A1 | 4/2016 | Evans et al. |

FOREIGN PATENT DOCUMENTS

| | | |
|---|---|---|
| EP | 0075444 A2 | 3/1983 |
| RU | 2488591 C2 | 7/2013 |
| WO | 9314125 A1 | 7/1993 |
| WO | 9429348 A2 | 12/1994 |
| WO | 2008100995 A1 | 8/2008 |
| WO | 2010129917 A2 | 11/2010 |
| WO | 2013033688 A1 | 3/2013 |
| WO | 2013148854 A1 | 10/2013 |

(Continued)

OTHER PUBLICATIONS

Hornig, et al., Experimental Dermatology 2016 vol. 25, pp. 831-838 (Year: 2016).*
Craddock, et al., Blood 2016 vol. 128, Issue 22 p. 1065 (Year: 2016).*
Vaccinex Presentation Report Slides, VX15.onc175 Exploring combinations with hydroxymate EMAs, Panobinostat and Belinostat in combination with SEMA4D-Blockade in the Colon26 Model, Feb. 19-Apr. 20, 2018 [Report updated Mar. 8, 2018], 4 slide pages.
Aurandt, J., Vikis, H. G., Gutkind, J. S., Ahn, N. and Guan, K. L. (2002). The semaphorin receptor plexin-B1 signals through a direct interaction with the Rho-specific nucleotide exchange factor, LARG. Proc. Natl. Acad. Sci. USA99,12085-12090.

(Continued)

*Primary Examiner* — Julie Wu
*Assistant Examiner* — John L Van Druff
(74) *Attorney, Agent, or Firm* — KDB Firm PLLC

(57) ABSTRACT

This disclosure provides a method for inhibiting, delaying, or reducing malignant cell growth in a subject with cancer, comprising administering to the subject a combination therapy comprising an effective amount of an isolated antibody or antigen-binding fragment thereof that specifically binds to semaphorin-4D (SEMA4D) and an effective amount of an epigenetic modulating agent, e.g., a histone deacetylase (HDAC) inhibitor (HDACi) a DNA methyltransferase (DNMT) inhibitor (DNMTi), or any combination thereof. The disclosure further provides a pharmaceutical composition comprising the combination therapy.

12 Claims, 11 Drawing Sheets

Specification includes a Sequence Listing.

(56) References Cited

FOREIGN PATENT DOCUMENTS

| WO | 2014209802 A1 | 12/2014 |
| WO | 2016010879 A1 | 1/2016 |
| WO | 2016054555 A2 | 4/2016 |

OTHER PUBLICATIONS

Barberis, D., Casazza, A., Sordella, R., Corso, S., Artigiani,S., Settleman, J., Comoglio, P. M. and Tamagnone, L. (2005). P190 Rho-GTPase activating protein associates with plexins and it is required for semaphorin signalling. J. Cell Sci.. 15,4689-4700.

Basile, J. R., Afkhami, T. and Gutkind, J. S.(2005). Semaphorin 4D/plexin-B1 induces endothelial cell migration through the activation of PYK2, Src, and the phosphatidylinositol 3-kinase-Akt pathway. Mol. Cell. Biol. 25,6889-6898.

Basile, J. R., Gavard, J. and Gutkind, J. S.(2007). Plexin-B1 utilizes RHOA and ROK to promote the integrin-dependent activation of AKT and ERK, and endothelial cell motility. J. Biol. Chem. 282,34888-34895.

Giordano, S., Corso, S., Conrotto, P., Artigiani, S., Gilestro,G., Barberis, D , Tamagnone, L. and Comoglio, P. M. (2002). The semaphorin 4D receptor controls invasive growth by coupling with Met. Nat. Cell Biol. 4,720-724.

Hirotani, M., Ohoka, Y., Yamamoto, T., Nirasawa, H., Furuyama,T., Kogo, M., Matsuya, T. and Inagaki, S. (2002). Interaction of plexin-B1 with PDZ domain-containing Rho guanine nucleotide exchange factors. Biochem. Biophys. Res. Commun. 297, 32-37.

Oinuma, I., Ishikawa, Y., Katoh, H. and Negishi, M.(2004). The Semaphorin 4D receptor Plexin-B1 is a GTPase activating protein for R-Ras. Science 305,862-865.

Perrot, V., Vazquez-Prado, J. and Gutkind, J. S.(2002). Plexin B regulates Rho through the guanine nucleotide exchange factors leukemia-associated Rho GEF (LARG) and PDZ-RhoGEF. J. Biol. Chem. 277,43115-43120.

Swiercz, J. M., Kuner, R. and Offermanns, S.(2004). Plexin-B1/RhoGEF-mediated RhoA activation involves the receptor tyrosine kinase ErbB-2. J. Cell Biol. 165,869-880.

Swiercz, J. M., Kuner, R., Behrens, J. and Offermanns, S.(2002). Plexin-B1 directly interacts with PDZ-RhoGEF/LARG to regulate RhoA and growth cone morphology. Neuron 35, 51-63.

Zabiewicz et al., "The Targeted Histone Deacetylase Inhibitor Tetinostat (CHR-2845) Shows Selective In Vitro Efficacy in Monocytoid-Lineage Acute Myeloid Leukaemia (AML)" Blood (2013) 122 (21): 1297.

Vikis, H. G., Li, W., He, Z. and Guan, K. L.(2000). The semaphorin receptor plexin-B1 specifically interacts with active Rac in a ligand-dependent manner. Proc. Natl. Acad. Sci. USA 97,12457-12462.

Sargeant et al., "OSU-HDAC42, a Histone Deacetylase Inhibitor, Blocks Prostate Tumor Progression in the Transgenic Adenocarcinoma of the Mouse Prostate Model" Cancer Research 68:3999-4009 (2008).

Arts et al., "JNJ-26481585, a Novel "Second-Generation" Oral Histone Deacetylase Inhibitor, Shows Broad-Spectrum Preclinical Antitumoral Activity".

Bracker et al., "Efficacy of MS-275, a selective inhibitor of class I histone deacetylases, in human colon cancer models" Journal of Oncology 35:909-920, 2009.

Brueckner, Bodo et al. "Epigenetic reactivation of tumor suppressor genes by a novel small-molecule inhibitor of human DNA methyltransferases." Cancer research vol. 65,14 (2005): 6305-11. doi:10.1158/0008-5472.CAN-04-2957.

Chothia et al., "Canonical Structures for the Hypervariable Regions of Immunoglobulins" J. Mol. Biol. (1987) 196. 901-917.

Chun SM, Lee JY, Choi J, Lee JH, Hwang JJ, et al. (2015) Epigenetic Modulation with HDAC Inhibitor CG200745 Induces Anti-Proliferation in Non-Small Cell Lung Cancer Cells. PLoS One 10(3): e0119379. https://doi.org/10.1371/journal.pone.0119379.

Cihák, A. "Biological effects of 5-azacytidine in eukaryotes." Oncology vol. 30,5 (1974): 405-22. doi:10.1159/000224981.

Dayhoff et al., "A Model of Evolutionary Change in Proteins" Atlas of Protein Sequence and Structure (Natl. Biomed. Res. Found., Washington, D.C.), 1978 pp. 345-352.

Elhabazi et al., "Biological Activity of Soluble CD100. I. The Extracellular Region of CD100 Is Released from the Surface of T Lymphocytes by Regulated Proteolysis" J Immunol Apr. 1, 2001, 166 (7) 4341-4347.

Fang et al., "Promoter hypermethylation and inactivation of O6-methylguanine-DNA methyltransferase in esophageal squamous cell carcinomas and its reactivation in cell lines" Journal of Oncology—Mar. 1, 2005 615-622.

Fournel et al., "MGCD0103, a novel isotype-selective histone deacetylase inhibitor, has broad spectrum antitumor activity in vitro and in vivo" Molecular Cancer Therapeutics—Apr. 2008 7:759-768.

Gameiro, Sofia R et al. "Inhibitors of histone deacetylase 1 reverse the immune evasion phenotype to enhance T-cell mediated lysis of prostate and breast carcinoma cells." Oncotarget vol. 7,7 (2016): 7390-402. doi:10.18632/oncotarget.7180.

Gang, A O et al. "5-Azacytidine treatment sensitizes tumor cells to T-cell mediated cytotoxicity and modulates NK cells in patients with myeloid malignancies." Blood cancer journal vol. 4,3 e197. Mar. 28, 2014, doi:10.1038/bcj.2014.14.

Giraudon, P., Vincent, P. & Vuaillat, C. T-cells in neuronal injury and repair. Neuromol Med 7, 207-216 (2005). https://doi.org/10.1385/NMM:7:3:207.

Goldsby et al., "Modeling Lean, Agile, and Leagile Supply Chain Strategies" Journal of Business Logistics—vol. 27, Issue1 pp. 57-80.

Göttlicher, M et al. "Valproic acid defines a novel class of HDAC inhibitors inducing differentiation of transformed cells." The EMBO journal vol. 20,24 (2001): 6969-78. doi:10.1093/emboj/20.24.6969.

Hérold, C et al. "Activation signals are delivered through two distinct epitopes of CD100, a unique 150 kDa human lymphocyte surface structure previously defined by BB18 mAb." International immunology vol. 7,1 (1995): 1-8. doi:10.1093/intimm/7.1.1.

Harlow et al., "Antibodies: A Laboratory Manual" Cold Spring Harbor Laboratory Press, 2nd ed. 1988—2 pages.

Ishida et al., "Involvement of CD100, a lymphocyte semaphorin, in the activation of the human immune system via CD72: implications for the regulation of immune and inflammatory responses" International Immunology, vol. 15, No. 8, pp. 1027-1034.

Juergens et al., "Combination Epigenetic Therapy Has Efficacy in Patients with Refractory Advanced Non-Small Cell Lung Cancer" Cancer Discovery—Dec. 2011—vol. 1, Issue 7.

Chothia et al., "Canonical structures for the hypervariable regions of immunoglobulins" vol. 196, Issue 4, Aug. 20, 1987, pp. 901-917.

Kantarjian et al., "Decitabine improves patient outcomes in myelodysplastic syndromes" vol. 106, Issue 8—Apr. 15, 2006—pp. 1794-1803.

Kato, Shingo et al. "Semaphorin 4D, a lymphocyte semaphorin, enhances tumor cell motility through binding its receptor, plexinB1, in pancreatic cancer." Cancer science vol. 102,11 (2011): 2029-37. doi:10.1111/j.1349-7006.2011.02053.x.

Kilsovic et al., "A Phase I Biological Study of MG98, an Oligodeoxynucleotide Antisense to DNA Methyltransferase 1, in Patients with High-Risk Myelodysplasia and Acute Myeloid Leukemia" Apr. 2008—vol. 14, Issue 8.

Kumanogoh and H. Kukutani, "The CD100-CD72 internation: a novel mechanism of immune regulation" Trends Immunol. Dec. 2001; 22 (12):670-6.

Kumanogoh et al., "Immune semaphorins: a new area of semaphorin research" Journal of Cell Science 116, 3463-3470 © 2003.

Lavelle, D., Saunthararajah, Y., Vaitkus, K. et al. S110, a novel decitabine dinucleotide, increases fetal hemoglobin levels in baboons (P. anubis). J Transl Med 8, 92 (2010). https://doi.org/10.1186/1479-5876-8-92.

Lee, Byron H et al. "Procainamide is a specific inhibitor of DNA methyltransferase 1." The Journal of biological chemistry vol. 280,49 (2005): 40749-56. doi:10.1074/jbc.M505593200.

Lee et al., "Development of a histone deacetylase 6 inhibitor and its biological effects" PNAS Sep. 24, 2013 110(39) 15704-15709.

(56) References Cited

OTHER PUBLICATIONS

Leoni, Flavio et al. "The histone deacetylase inhibitor ITF2357 reduces production of pro-inflammatory cytokines in vitro and systemic inflammation in vivo." Molecular medicine (Cambridge, Mass.) vol. 11,1-12 (2005): 1-15. doi:10.2119/2006-00005. Dinarello.
Li, Huili et al. "Immune regulation by low doses of the DNA methyltransferase inhibitor 5-azacitidine in common human epithelial cancers." Oncotarget vol. 5,3 (2014): 587-98. doi:10.18632/oncotarget.1782.
Li, Y, and T O Tollefsbol. "Impact on DNA methylation in cancer prevention and therapy by bioactive dietary components." Current medicinal chemistry vol. 17,20 (2010): 2141-51. doi:10.2174/092986710791299966.
Lin, Tzu-Yin et al. "AR-42, a novel HDAC inhibitor, exhibits biologic activity against malignant mast cell lines via down-regulation of constitutively activated Kit." Blood vol. 115,21 (2010): 4217-25. doi:10.1182/blood-2009-07-231985.
Lizée, Gregory et al. "Harnessing the power of the immune system to target cancer." Annual review of medicine vol. 64 (2013): 71-90. doi:10.1146/annurev-med-112311-083918.
Mandl-Weber et al., "The novel inhibitor of histone deacetylase resminostat (RAS2410) inhibits proliferation and induces apoptosis in multiple myeloma (MM) cells" vol. 149, Issue 4—May 2010— pp. 518-528.
Moffat et al., "Discovery of 2-(6-{[(6-Fluoroquinolin-2-yl)methyl]amino}bicyclo[3.1.0]hex-3-yl)-N-hydroxypyrimidine-5-carboxamide (CHR-3996), a Class I Selective Orally Active Histone Deacetylase Inhibitor" J. Med. Chem. 2010, 53, 24, 8663-8678— Publication Date:Nov. 16, 2010.
Nakajima et al., "FR901228, a Potent Antitumor Antibiotic, Is a Novel Histone Deacetylase Inhibitor" vol. 241, Issue 1, May 25, 1998, pp. 126-133.
Niesvizky et al., "ACY-241, a Novel, HDAC6 Selective Inhibitor: Synergy with Immunomodulatory (IMiD®) Drugs in Multiple Myeloma (MM) Cells and Early Clinical Results (ACE-MM-200 Study)" Blood (2015) 126 (23): 3040.
International Search Report and Written Opinion for Application No. PCT/US2020/041549, dated Sep. 8, 2020, 32 pages.
Xing-Dong Xu et al., "Suberoylanilide hydroxamic acid, an inhibitor of histone deacetylase, suppresses vasculogenic mimicry and profileration of highly aggressive pancreatic cancer PaTu8988 cells", BMC Cancer, Biomed Central, London, GB, vol. 14, No. 1, May 27, 2014, p. 373.
Tomas Eckschlager et al., "Histone Deacetylase Inhibitors as Anticancer Drugs", International Journal of Molecular Sciences, vol. 18, No. 7, Jul. 1, 2017, p. 1414.
Suzuki et al., "Semaphorins and their receptors in immune cell interactions", Nature Immunology, 2008 Nature Publishing, 7 pages.
Evans et al., "Antibody Blockage of Semaphorin 4D Promotes Immune Infiltration into Tumor and Enhances Response to Other Immunomodulatory Therapies" Cancer Immunology Research, 2015, 689-702.
Ch'ng et a., "Prognostic Significance of CD100 Expression in Soft Tissue Sarcoma" 2007, American Cancer Society, 9 pages.
Campos et al., "Ki-67 and CD100 immunohistochemical expression is associated with local recurrence and poor prognosis in soft tissue sarcomas, respectively", Oncology Letters 5:1527-35 (2013).
Conrotto et al., "Sema4D induces angiogenesis through Met recruitment by Plexin B1" Blood Journal, Jun. 1, 2005, vol. 105, No. 11, 9 pages.
Basile et al., "Plexin-B1 Utilizes RhoA and Rho Kinase to Promote the Integrin-dependent Activation of Akt and ERK and Endothelial Cell Motility" Journal of Biological Chemical vol. 282, No. 48, pp. 34888-34895, Nov. 30, 2007.
Sierra et al., "Tumor angiogenesis and progression are enhanced by Sema4D produced by tumor-associated macrophages" Exp Med (2008) 205 (7): 1673-1685.

Brummell, D.A., et al., "Probing the combining site of an anti-carbohydrate antibody by saturation-mutagenesis: Role of the heavy-chain CDR3 residues", Biochem. 32(4):1180-1187 (1993) Abstract.
Kobayashi et al., "Tryptophan H33 plays an important role in pyrimidine (6-4) pyrimidone photoproduct binding by a high-affinity antibody", Protein Eng. 12(10):879-884 (1999).
Burks, E.A., et al., "In vitro scanning saturation mutagenesis of an antibody binding pocket", Proc. Natl. Acad Sci. USA 94:.412-417 (1997).
Strohlein and Heiss, "The trifunctional antibody catumaxomab in treatment of malignant ascites and peritoneal carcinomatosis", Future Oncol. 6(9):1387-94 (2010) Abstract.
Mabry, R., and Snavely, M., "Therapeutic bispecific antibodies: The selection of stable single-chain fragments to overcome engineering obstacles", IDrugs. 13(8):543-9 (2010) Abstract.
Kruger et al., "Semaphorins command cells to move", Nature Rev. Mol. Cell Biol. 6:789-800 (2005).
Pasterkamp, R.J., "R-Ras fills another GAP in semaphorin signaling", Trends in Cell Biology 15(2):61-64 (2005) Abstract.
Kumanogoh et al., "Identification of CD72 as a Lymphocyte Receptor for the Class IV Semaphorin CD100: A novel Mechanism for Regulating B Cell Signaling", Immunity 13:621-631 (2000) Abstract.
Watanabe et al., "Enhanced Immune Responses in Transgenic Mice Expressing a Truncated Form of the Lymphocyte Semaphorin CD100 1", J Immunol 167:4321-4328 (2001).
Kunkel, T.A., "Rapid and efficient site-specific mutagenesis without phenotypic selection", Proc. Natl. Acad. Sci. USA 82:488-492 (1985).
Kunkel et al., "Rapid and Efficient Site-Specific Mutagenesis without Phenotypic Selction", Methods Enzymol. 154:367-382 (1987) Abstract.
Shi et al., "The Class IV Semaphorin CD 100 Plays Nonredundant Roles in the Immune System: Defective B and T Cell Activation in CD100-Deficient Mice", Immunity 13:633-642 (2000).
Kumanogoh et al., "Requirement for the Lymphocyte Semaphorin, CD100, in the Induction of Antigen-Specific T Cells and the Maturation of Dendritic Cells", J Immunol 169:1175-1181 (2002).
Wang et al., "Functional soluble CD100/Sema4D released from activated lymphocytes: possible role in normal and pathologic immune responses", Blood 97(11):3498-3504 (2001) Abstract.
Giraudon et al., "Semaphorin CD100 from Activated T Lymphocytes Induces Process Extension Collapse in Oligodendrocytes and Death of Immature Neural Cells", J Immunol. 172:1246-1255 (2004).
Smith and Waterman, "Comparison of Biosequences", Adv. Appl. Math. 2:482-489 (1981).
Maio et al., "Molecular Pathways: At the Crossroads of Cancer Epigenetics and Immunotherapy" Clin Cancer Res; 21(18) Sep. 15, 2015, pp. 4040-4047.
Mottamal et al., "Histone Deacetylase Inhibitors in Clinical Studies as Templates for New Anticancer Agents" Molecules 2015, 20, 3898-3941.
Gravina et al., "Biological rationale for the use of DNA methyltransferase inhibitors as new strategy for modulation of tumor response to chemotherapy and radiation".
Berger et al., "An operational definition of epigenetics" Genes Dev. Apr. 1, 2009; 23(7): 781-783.
Drummond et al., "Clinical Development of Histone Deacetylase Inhibitors as Anticancer Agents" Annual Review of Pharmacology and Toxicology, vol. 45:495-528, Sep. 2005—Abstract.
Porcu et al., "The emerging therapeutic potential of sirtuin-interacting drugs: from cell death to lifespan extension" Trends Pharmacol Sci. Feb. 2005;26(2):94-103 Abstract.
Stresemann et al., "Modes of action of the DNA methyltransferase inhibitors azacytidine and decitabine" Int. J. Cancer: 123, 8-13 (2008).
Zhou et al., "Semaphorin 4D cooperates with VEGF to promote angiogenesis and tumor progression" Angiogenesis. Sep. 2012; 15(3):391-407.
Kikutani et al., "Semaphorins in interactions between T cells and antigen-presenting cells", Nature Rev Immunol 3:159-167 (2003).

(56) References Cited

OTHER PUBLICATIONS

Chueh et al., "Mechanisms of Histone Deacetylase Inhibitor-Regulated Gene Expression in Cancer Cells" Antioxid Redox Signal. Jul. 1, 2015; 23(1): 66-84.

Gnyszka et al., "DNA Methyltransferase Inhibitors and Their Emerging Role in Epigenetic Therapy of Cancer" Anticancer Research 33: 2989-2996 (2013).

Delaire et al., "Biological Activity of Soluble CD100. II. Soluble CD100, Similarly to H-SemaIII, Inhibits Immune Cell Migration" J Immunol 2001; 166:4348-4354.

Sambrook et al. (1989) Molecular Cloning: A Laboratory Manual (Cold Spring Harbor, N.Y.).

Phiel, C J et al. "Histone deacetylase is a direct target of valproic acid, a potent anticonvulsant, mood stabilizer, and teratogen." The Journal of biological chemistry vol. 276,39 (2001): 36734-41. doi:10.1074/jbc.M101287200.

Plump et al., "Pharmacodynamic Response and Inhibition of Growth of Human Tumor Xenografts by the Novel Histone Deacetylase Inhibitor PXD101" Molecular Cancer Therapies—Aug. 2003—vol. 2, Issue 8.

Qiao et al., "Synergistic antitumor activity of gemcitabine combined with triptolide in pancreatic cancer cells" Oncology Letters—vol. 11 Issue 5—3527-3533.

Roulois et al., "DNA-Demethylating Agents Target Colorectal Cancer Cells by Inducing Viral Mimicry by Endogenous Franscripts" Cell—vol. 162, Issue 5, Aug. 27, 2015, pp. 961-973.

Santo, Loredana et al. "Preclinical activity, pharmacodynamic, and pharmacokinetic properties of a selective HDAC6 inhibitor, ACY-1215, in combination with bortezomib in multiple myeloma." Blood vol. 119,11 (2012): 2579-89. doi:10.1182/blood-2011-10-387365.

Tamagnone, L et al. "Plexins are a large family of receptors for transmembrane, secreted, and GPI-anchored semaphorins in vertebrates." Cell vol. 99,1 (1999): 71-80. doi:10.1016/s0092-8674(00)80063-x.

Witherden et al., "The CD100 Receptor Interacts with Its Plexin B2 Ligand to Regulate Epidermal γδ T Cell Function" Immunity—vol. 37, Issue 2, Aug. 24, 2012, pp. 314-325.

Wrangle, John et al. "Alterations of immune response of Non-Small Cell Lung Cancer with Azacytidine." Oncotarget vol. 4,11 (2013): 2067-79. doi:10.18632/oncotarget.1542.

Yee, Donald L et al. "Aggregometry detects platelet hyperreactivity in healthy individuals." Blood vol. 106,8 (2005): 2723-9. doi:10.1182/blood-2005-03-1290.

Zambrano, P., Segura-Pacheco, B., Perez-Cardenas, E. et al. A phase I study of hydralazine to demethylate and reactivate the expression of tumor suppressor genes. BMC Cancer 5, 44 (2005).

Zhijun, H., Shusheng, W., Han, M. et al. Pre-clinical characterization of 4SC-202, a novel class I HDAC inhibitor, against colorectal cancer cells. Tumor Biol. 37, 10257-10267 (2016).

Zhou et al., "Zebularine: A Novel DNA Methylation Inhibitor that Forms a Covalent Complex with DNA Methyltransferases" Journal of Molecular Biology—vol. 321, Issue 4, Aug. 23, 2002, pp. 591-599.

Baird, Anne-Marie, et al., "Improving lung cancer immunotherapy using epigenetic approaches" BMN—Blog Network—Mar. 26, 2015, 6 pages.

Lin, Tzu-Yin et al. "AR-42, a novel HDAC inhibitor, exhibits biologic activity against malignant mast cell lines via down-regulation of constitutively activated Kit." Blood vol. 115,21 (2010): 4217-2. doi:10.1182/blood-2009-07-231985.

Buggy et al., "CRA-024781: A novel synthetic inhibitor of histone deacetylase enzymes with antitumor activity in vitro and in vivo", Mol. Cancer Ther. 5(5):1309-17 (2006). DOI:10.1158/1535-7163. MCT-05-0442.

Lai et al., "CUDC-101, a multitargeted inhibitor of histone deacetylase, epidermal growth factor receptor, and human epidermal growth factor receptor 2, exerts potent anticancer activity", Cancer Res. 70(9):3647-56 (2010). doi 10.1158/0008-5472.

Novotny-Diermayr et al., "SB939, a novel potent and orally active histone deacetylase inhibitor with high tumor exposure and efficacy in mouse models of colorectal cancer", Mol Cancer Ther. 9(3):642-52 (2010). doi:10.1158/1535-7163.

Qiao et al., "Synergistic antitumor activity of gemcitabine combined with triptolide in pancreatic cancer cells", Onco Lett 11(5):3527-3533 (2016).

Shen et al., "Class I Histone Deacetylase Inhibitor Entinostat Supresses Regulatory T Cells and Enhances Immunotherapies in Renal and Prostate Cancer Models", PLoS One, 2012, vol. 7, Issue 1, e30815, pp. 1-14.

\* cited by examiner

TREATMENT OF CANCER WITH A SEMAPHORIN-4D ANTIBODY IN COMBINATION WITH AN EPIGENETIC MODULATING AGENT

CROSS-REFERENCE TO RELATED APPLICATIONS

This application is a US National Stage Entry of PCT Application No. PCT/US2018/022414, filed Mar. 14, 2018, which claims the benefit of U.S. Provisional Patent Application Ser. No. 62/473,731, filed Mar. 20, 2017, which are each hereby incorporated by reference in their entireties.

SEQUENCE LISTING STATEMENT

The content of the electronically submitted sequence listing in ASCII text file (Name: 58008_172854_Seq-List_ST25.txt; Size: 5936 bytes; Date of Creation: Feb. 28, 2018) filed with the application is incorporated herein by reference in its entirety.

BACKGROUND

Semaphorin 4D (SEMA4D), also known as CD100, is a transmembrane protein that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., *Nature Rev. Immunol.* 3:159-167 (2003); Kikutani et al., *Nature Immunol.* 9:17-23 (2008).

SEMA4D is expressed at high levels in lymphoid organs, including the spleen, thymus, and lymph nodes, and in non-lymphoid organs, such as the brain and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various immunological stimuli. The release of soluble SEMA4D from immune cells is also increased by cell activation. SEMA4D has been implicated in the development of certain cancers (Ch'ng et al., *Cancer* 110:164-72 (2007); Campos et al., *Oncology Letters* 5:1527-35 (2013); Kato et al., *Cancer Sci.* 102:2029-37 (2011)) and several reports suggest that one mechanism of this influence is the role of SEMA4D in promoting tumor angiogenesis (Conrotto et al., *Blood* 105:4321-4329 (2005). Basile et al., *J Biol. Chem.* 282: 34888-34895 (2007); Sierra et. al. *J. Exp. Med.* 205:1673 (2008); Zhou et al., *Angiogenesis* 15:391-407 (2012)). Tumor growth and metastasis involve a complex process of cross talk amongst the tumor cells, stroma and immune infiltrate, as well as the endothelial cells and vasculature. SEMA4D is over-expressed in a wide array of tumor types and is also produced by inflammatory cells recruited to the tumor microenvironment. Recent work suggests that SEMA4D plays a role in migration, survival, differentiation and organization of the different cell types that constitute the tumor stroma (Evans et al., *Cancer Immunol. Res.* 3:689-701 (2015)).

Cancer cells can adapt to avoid host immune recognition through modification of gene expression via epigenetic mechanisms, without altering the sequence of the genomic DNA. Epigenetic mechanisms largely center on alterations of genomic DNA methylation and posttranslational modifications of histones, resulting in, e.g., alterations in chromatin structure and availability of DNA for transcription. Through these epigenetic mechanisms cancer cells can establish altered, heritable gene-expression profiles that promote proliferation and immune evasion. See, e.g., Maio, et al., *Clin. Cancer Res.* 21:4040-4047 (2015).

Cells can control the coiling and uncoiling of DNA around histones via histone acetyl transferases (HAT), which acetylate the lysine residues in core histones leading to a less compact and more transcriptionally active chromatin and histone deacetylases (HDAC), which remove the acetyl groups from the lysine residues leading to the formation of a condensed and transcriptionally silenced chromatin. Modulation of HAT/HDAC activity by tumor cells can results in extensive epigenetic modulation of gene expression in tumor cells, allowing the cells to evade surveillance by the patient's immune system. See, e.g., Maio, et al., *Clin. Cancer Res.* 21:4040-4047 (2015).

Histone deacetylase inhibitors (HDACi (used herein both as the singular and the plural)) have emerged as cancer therapeutic agents. HDACi can inhibit the proliferation of tumor cells by inducing extensive transcriptional changes, activating and/or repressing various genes through modulating the acetylation/deacetylation of histones and/or non-histone proteins such as transcription factors. Chueh, A. C., et al, *Antioxidants & Redox Signaling* 23:66-84 (2015). HDACi can interfere with cell proliferation and survival, e.g., with cell cycle, differentiation, and apoptosis of cancer cells. HDACi can also enhance immunogenicity and antigen presentation by tumor cells and provides rationale for combining HDACi with immunotherapy (Gameiro S R et al., *Oncotarget* 7:7390-7402 (2016)). Several compounds are currently in early phase clinical development as potential treatments for solid and hematological cancers both as monotherapy and in combination with cytotoxics and differentiation agents. See, e.g., Mottamal, M., et al., *Molecules* 20:3898-3941 (2015).

Methylation of genomic DNA is an extensively characterized epigenetic modification. Methylation of DNA leads to transcriptional quiescence, resulting in gene silencing. Gravina G. L., et al., *Mol. Cancer* 9:305-320 (2010). Methylation is facilitated by DNA methyltransferases (DNMTs), which catalyze the addition of a methyl group to the 5' carbon of cytosine residues. Id. Hypermethylated DNA is common in tumor and other cancer cells. A variety of DNA methyltransferase inhibitors (DNMTi (used herein both as the singular and the plural)) are currently in use or are being tested for treatment of various cancers. These include deoxyribonucleoside analogs such as azacytidine, and non-nucleoside analogs such as antisense oligonucleotides and small molecule enzyme inhibitors. Id.

SUMMARY

This disclosure provides a method for inhibiting, delaying, or reducing malignant cell growth in a subject with cancer, where the method includes administering to the subject a combination therapy including an effective amount of an isolated antibody or antigen-binding fragment thereof that specifically binds to semaphorin-4D (SEMA4D) and an effective amount of an epigenetic modulating agent. According to the provided method, the anti-SEMA4D antibody or fragment thereof can inhibit SEMA4D interaction with its receptor, e.g., Plexin-B1, Plexin-B2, or CD72. For example, according to the provided method the anti-SEMA4D antibody or fragment thereof can inhibit SEMA4D-mediated Plexin-B1 signal transduction.

In certain aspects, the anti-SEMA4D antibody or fragment thereof includes a variable heavy chain (VH) that includes VH CDRs 1-3 having the amino acid sequences SEQ ID NOS: 2, 3, and 4, respectively, and a variable light chain (VL) that includes VL CDRs 1-3 having the amino acid sequences SEQ ID NOS: 6, 7, and 8, respectively. In certain aspects the amino acid sequences of the VH and VL include, respectively, SEQ ID NO: 1 and SEQ ID NO: 5, or SEQ ID NO: 9 and SEQ ID NO: 10.

In certain aspects, the epigenetic modulating agent can include a histone deacetylase (HDAC) inhibitor (HDACi), a DNA methyltransferase (DNMT) inhibitor (DNMTi), or any combination thereof.

In certain aspects, the epigenetic modulating agent can include a histone deacetylase (HDAC) inhibitor (HDACi). In certain aspects the HDAC can be a Class I HDAC, a Class IIA HDAC, a Class IIB HDAC, a Class IV HDAC, or any combination thereof, or the HDAC can include a zinc-containing catalytic domain. In certain aspects, the HDACi can bind to the zinc-containing catalytic domain of the HDAC. In certain aspects, the HDACi can include a chemical moiety selected from the group consisting of a hydroxamic acid or a salt thereof, a cyclic tetrapeptide, a depsipeptide, a benzamide, an electrophilic ketone, an aliphatic acid or a salt thereof, or any combination thereof. For example, in certain aspects, the HDACi can be Vorinostat, Romidepsin, Chidamide, Panobinostat, Belinostat, Valproic acid or a salt thereof, Mocetinostat, Abexinostat, Entinostat, Pracinostat, Resminostat, Givinostat, Quisinostat, Kevetrin, CUDC-101, AR-42, Tefinostat (CHR-2845), CHR-3996, 4SC-202, CG200745, ACY-1215, ACY-241, any combination thereof, or any salt, crystal, amorphous structure, hydrate, derivative, metabolite, isomer, or prodrug thereof. In certain aspects, the HDACi is Entinostat (Pyridin-3-ylmethyl N-[[4-[(2-aminophenyl)carbamoyl]phenyl]methyl]carbamate).

In certain aspects, the epigenetic modulating agent can include a DNA methyltransferase (DNMT) inhibitor (DNMTi). In certain aspects the DNMT can be DNMT1, DNMT-3a, DNMT-3b, or any combination thereof. In certain aspects, the DNMTi can be a nucleoside analog, an antisense oligonucleotide, a small molecule enzyme inhibitor, or any combination thereof. For example, in certain aspects the DNMTi can be azacytidine, decitabine, zebularine, SGI-110, epigallocatechin gallate, MG98, RG108, procainamide, hydralazine, any combination thereof, or any salt, crystal, amorphous structure, hydrate, derivative, metabolite, isomer, or prodrug thereof. In certain aspects the DNMTi is azacytidine.

In a particular aspect of the provided method, the isolated antibody or antigen-binding fragment thereof that specifically binds to semaphorin-4D (SEMA4D) comprises a VH comprising the amino acid sequence SEQ ID NO: 1 and a VL comprising the amino acid sequence SEQ ID NO: 5, and the epigenetic modulating agent comprises the HDACi Entinostat. In another particular aspect of the provided method, the isolated antibody or antigen-binding fragment thereof that specifically binds to semaphorin-4D (SEMA4D) comprises a VH comprising the amino acid sequence SEQ ID NO: 1 and a VL comprising the amino acid sequence SEQ ID NO: 5, and the epigenetic modulating agent comprises the DNMTi azacytidine.

According to the provided method, the antibody or antigen-binding fragment thereof and the epigenetic modulating agent can be administered separately, or they can be administered simultaneously.

In certain aspects of the provided method, administration of the combination therapy can result in enhanced therapeutic efficacy relative to administration of the antibody or fragment thereof or the epigenetic modulating agent alone. For example, in certain aspects the enhanced therapeutic efficacy is greater than an additive effect, e.g., a synergistic effect.

In certain aspects of the provided method, the cancer to be treated can be a solid tumor, a hematological malignancy, any metastasis thereof, or any combination thereof. In certain aspects, the solid tumor can be, e.g., a sarcoma, a carcinoma, a melanoma, any metastases thereof, or any combination thereof. More specifically, the solid tumor can be, e.g., squamous cell carcinoma, adenocarcinoma, basal cell carcinoma, renal cell carcinoma, ductal carcinoma of the breast, soft tissue sarcoma, osteosarcoma, melanoma, small-cell lung cancer, non-small cell lung cancer, adenocarcinoma of the lung, cancer of the peritoneum, hepatocellular carcinoma, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, any metastases thereof, or any combination thereof.

In certain aspects of the provided method, the cancer to be treated can be a hematologic malignancy or metastasis thereof. In certain aspects, the hematologic malignancy can be leukemia, lymphoma, myeloma, acute myeloid leukemia, chronic myeloid leukemia, acute lymphocytic leukemia, chronic lymphocytic leukemia, hairy cell leukemia, Hodgkin lymphoma, non-Hodgkin lymphoma, multiple myeloma, any metastases thereof, or any combination thereof.

In certain aspects, the method provided herein can further include administration of an additional cancer therapy, e.g., surgery, chemotherapy, radiation therapy, a cancer vaccine, administration of an immunostimulatory agent, adoptive T cell or antibody therapy, administration of an immune checkpoint blockade inhibitor, administration of a regulatory T cell (Treg) modulator, and a combination thereof.

This disclosure further provides a pharmaceutical composition that includes an effective amount of an isolated antibody or antigen-binding fragment thereof that specifically binds to semaphorin-4D (SEMA4D) and an effective amount of an epigenetic modulating agent. In certain aspects, the pharmaceutical composition can further include a carrier, an excipient, or any combination thereof.

In certain aspects, the antibody or fragment thereof of the provided composition can include a variable heavy chain (VH) comprising VH CDRs 1-3 comprising SEQ ID NOS: 2, 3, and 4, respectively, and a variable light chain (VL) comprising VL CDRs 1-3 comprising SEQ ID NOS: 6, 7, and 8, respectively. In certain aspects, the antibody or fragment thereof of the provided composition can include a VH and VL that include, respectively, SEQ ID NO: 1 and SEQ ID NO: 5, or SEQ ID NO: 9 and SEQ ID NO: 10.

In certain aspects, the epigenetic modulating agent included in the provided pharmaceutical composition can include a histone deacetylase (HDAC) inhibitor (HDACi), a DNA methyltransferase (DNMT) inhibitor (DNMTi), or any combination thereof.

Where the composition includes a HDACi, the HDACi can be, e.g., Vorinostat, Romidepsin, Chidamide, Panobinostat, Belinostat, Valproic acid or a salt thereof, Mocetinostat, Abexinostat, Entinostat, Pracinostat, Resminostat, Givinostat, Quisinostat, Kevetrin, CUDC-101, AR-42, Tefinostat (CHR-2845), CHR-3996, 4SC-202, CG200745, ACY-1215, ACY-241, any combination thereof, or any salt, crystal, amorphous structure, hydrate, derivative, metabolite, isomer, or prodrug thereof. In certain aspects the HDACi can be Entinostat (Pyridin-3-ylmethyl N-[[4-[(2-aminophenyl)carbamoyl]phenyl]methyl]carbamate).

Where the composition includes a DNMTi, the DNMTi can be, e.g., azacytidine, decitabine, zebularine, SGI-110, epigallocatechin gallate, MG98, RG108, procainamide, hydralazine, any combination thereof, or any salt, crystal, amorphous structure, hydrate, derivative, metabolite, isomer, or prodrug thereof. In certain aspects the DNMTi can be azacytidine.

In a particular aspect, the disclosure provides a pharmaceutical composition that includes an effective amount of an isolated antibody or antigen-binding fragment thereof that specifically binds to semaphorin-4D (SEMA4D), where the antibody or fragment thereof includes the VH amino acid sequence SEQ ID NO: 1 and the VL amino acid sequence SEQ ID NO: 5; and an effective amount of the HDACi Entinostat. in another particular aspect, the disclosure provides a pharmaceutical composition that includes an effective amount of an isolated antibody or antigen-binding fragment thereof that specifically binds to semaphorin-4D (SEMA4D), where the antibody or fragment thereof includes the VH amino acid sequence SEQ ID NO: 1 and the VL amino acid sequence SEQ ID NO: 5; and an effective amount of the DNMTi azacytidine.

BRIEF DESCRIPTION OF THE DRAWINGS/FIGURES

Figure 2A:
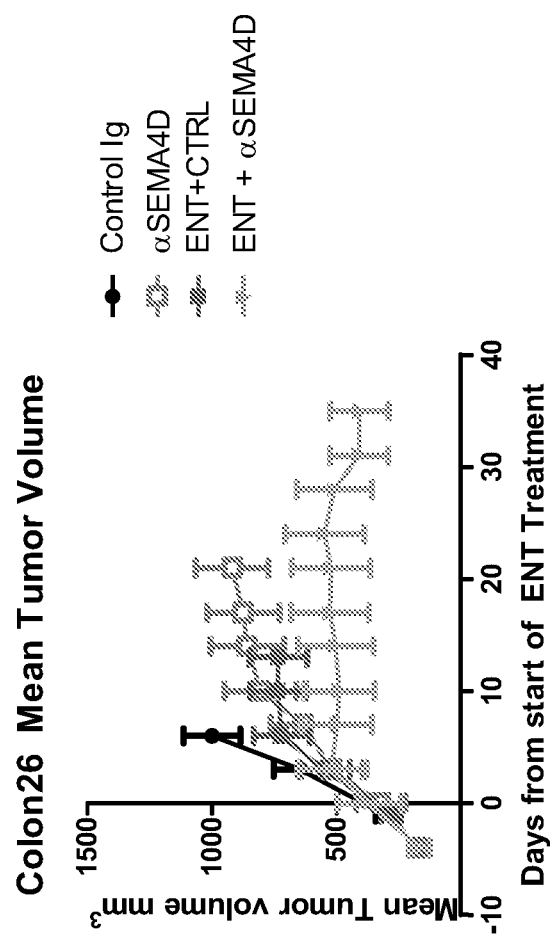
FIG. 2A shows the mean tumor volume over time for the various treatments in Example 1.
Figure 2B:
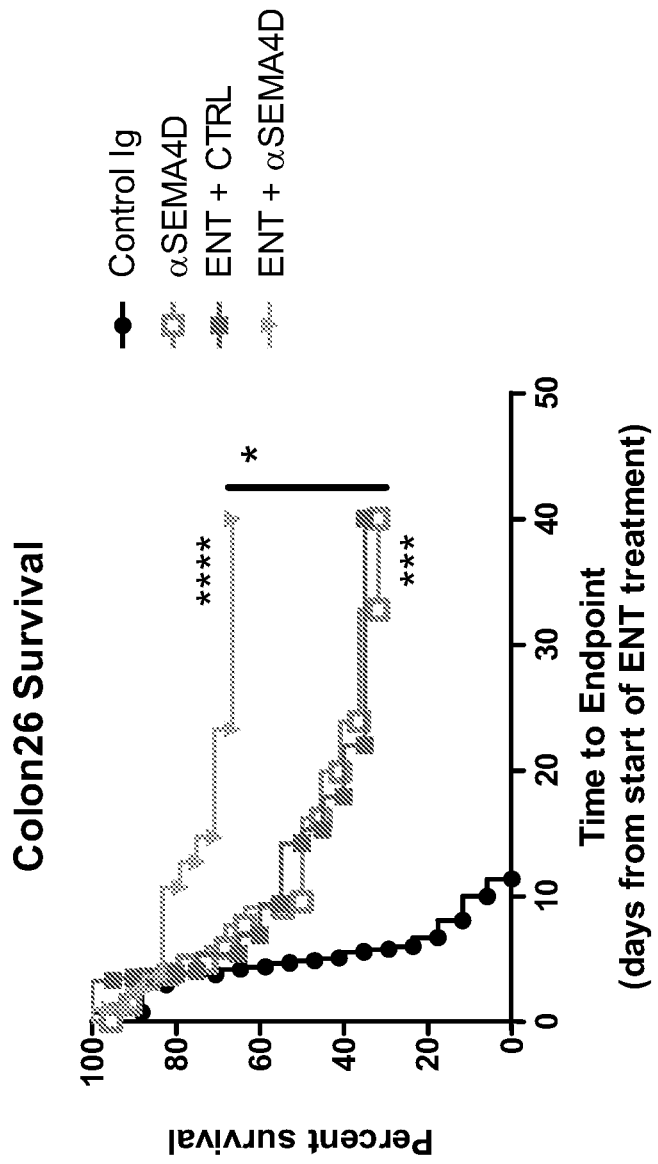

FIG. 2B shows percent survival over time for the various treatments in Example 1. Statistical significance was determined using Mantel Cox Log Rank test. Prism reports results as non-significant (ns) at P>0.05, significant (symbolized by "*") at $0.01<P\leq0.05$, very significant ("") at $0.001<P\leq0.01$, and extremely significant ("*") at $P\leq0.001$ or ("****") at $P\leq0.0001$.

Figure 2C:
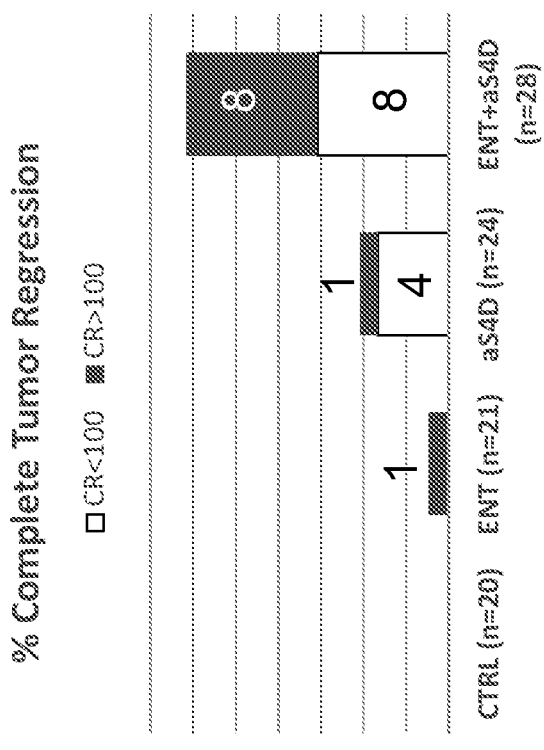

FIG. 2C is a bar graph showing the percent of complete tumor regression (tumor volume <50 mm$^3$) for the various treatments in Example 1. Statistical significance was determined using Fisher's exact test, Prism reports results as non-significant (ns) at P>0.05, significant (symbolized by "*") at $0.01<P\leq0.05$, very significant ("") at $0.001<P\leq0.01$, and extremely significant ("*") at $P\leq0.001$ or ("****") at $P\leq0.0001$.

Figure 2D:
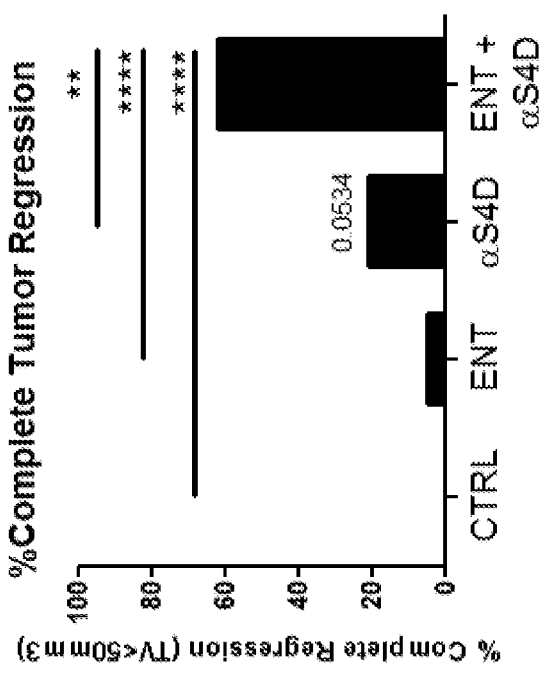

FIG. 2D shows the same data as FIG. 2C, stratified as to whether or not the tumor exceeded at least 100 mm$^3$ before regressing.

Figure 3A:
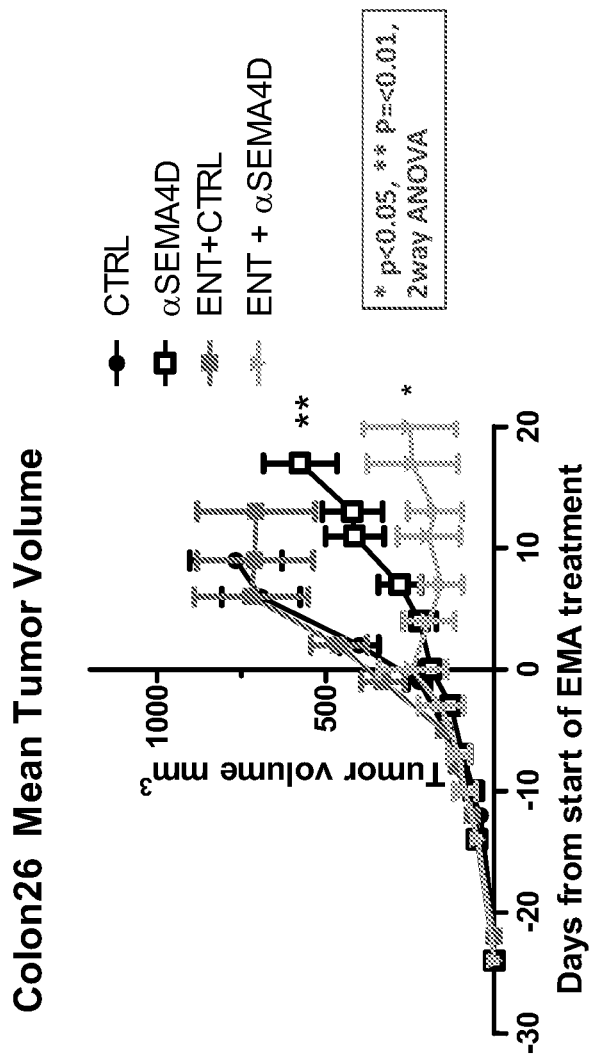
Figure 3B:
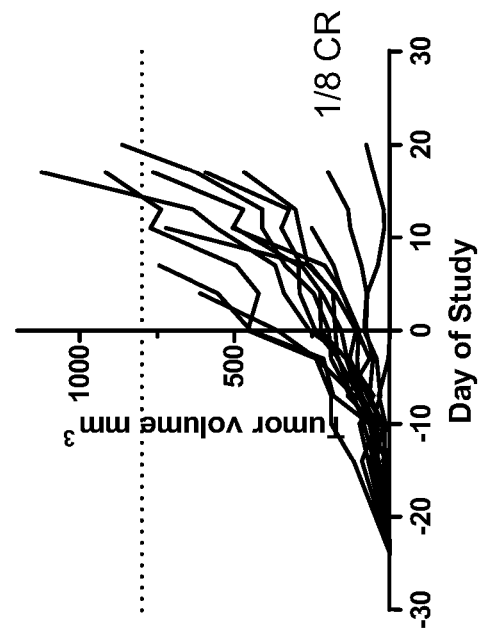

FIG. 3A shows mean tumor volume over time for the various treatments in Example 2. Statistical significance was determined using 2-way ANOVA. Prism reports results as non-significant (ns) at P>0.05, significant (symbolized by "*") at $0.01<P\leq0.05$, very significant ("**") at $0.001<P\leq0.01$ FIG. 3B shows tumor volume for individual control animals over time in Example 2.

Figure 3C:
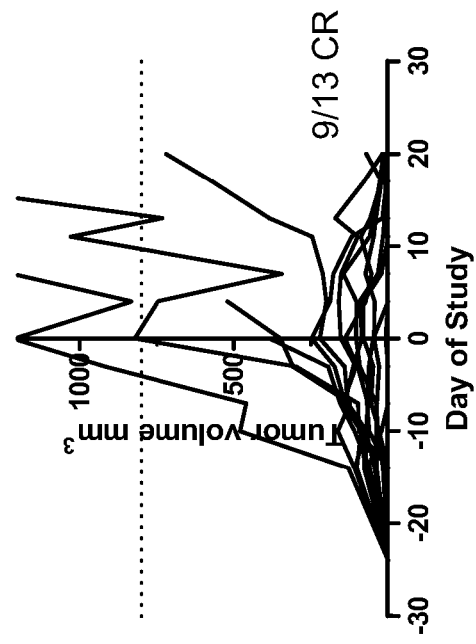

FIG. 3C shows tumor volume for individual animals treated with anti-SEMA4D antibody over time in Example 2.

Figure 3D:
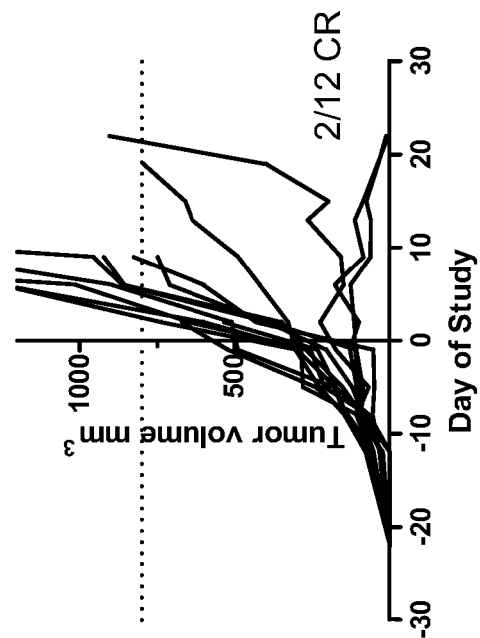

FIG. 3D shows tumor volume for individual animals treated with Entinostat (ENT) and control antibody over time in Example 2.

Figure 3E:
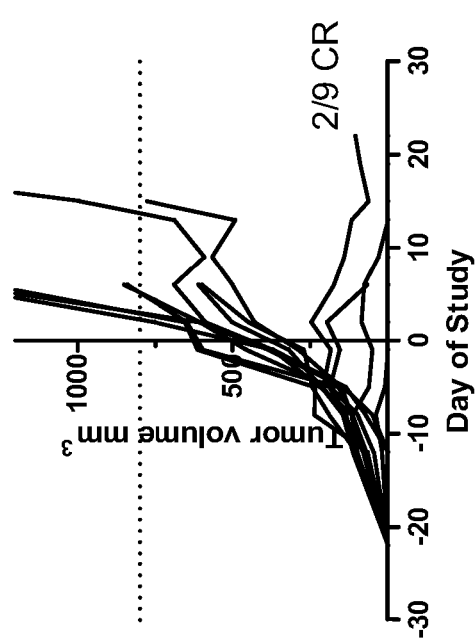

FIG. 3E shows tumor volume for individual animals treated with ENT and anti-SEMA4D antibody over time in Example 2.

Figure 3F:
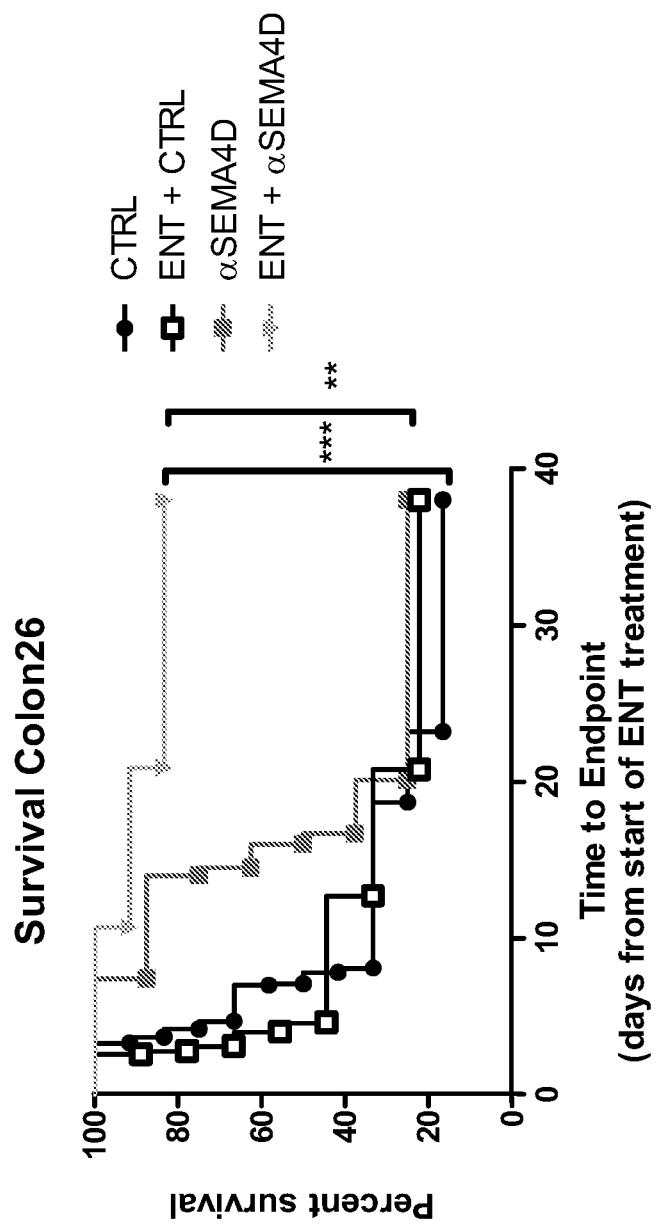

FIG. 3F shows percent survival over time for the various treatments in Example 2. Statistical significance was determined using the Mantel Cox Log Rank test. Prism reports results as significant (symbolized by "*") at $0.01<P\leq0.05$ and very significant ("**") at $0.001<P\leq0.01$.

Figure 4:
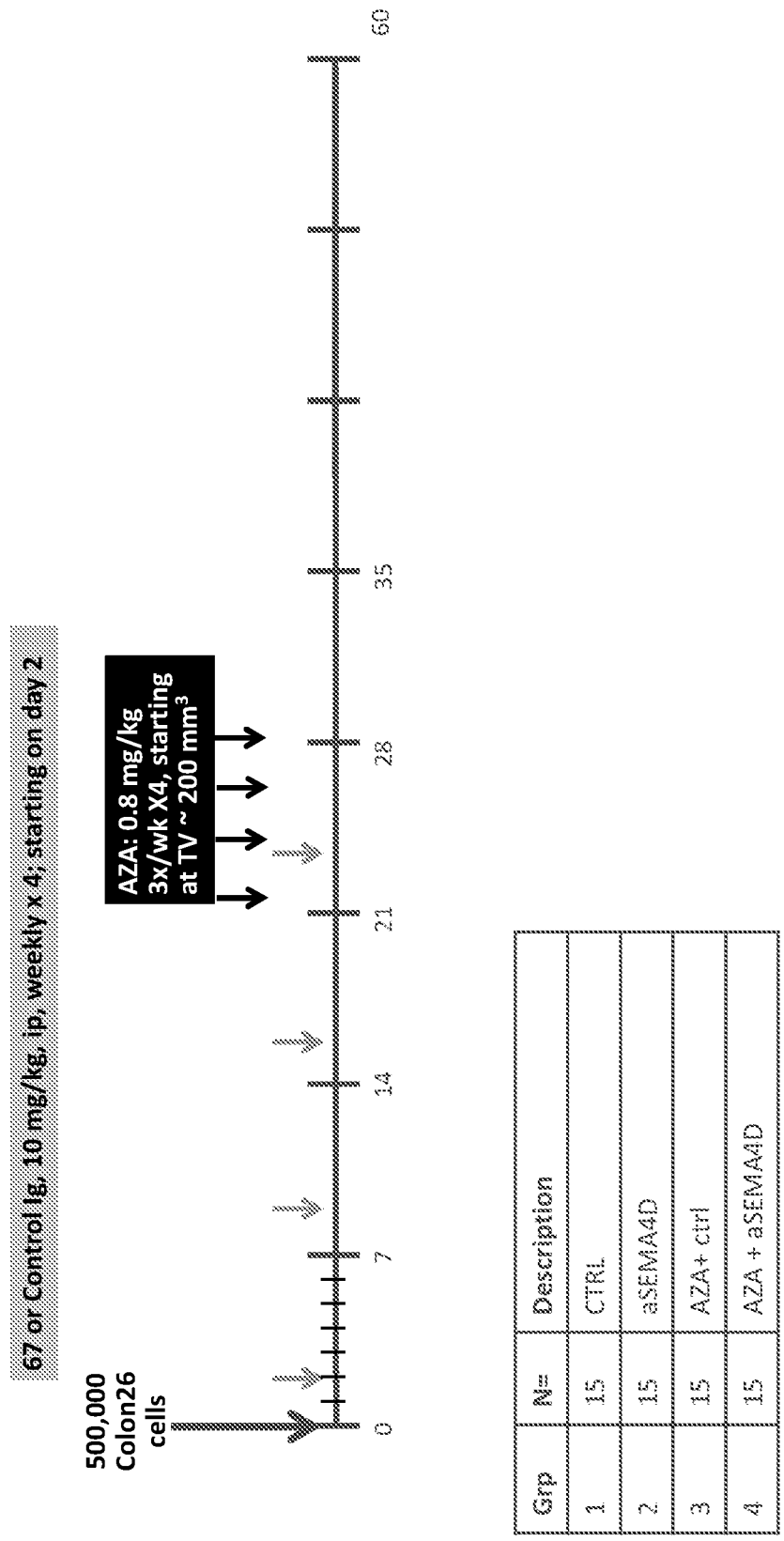

FIG. 4 shows the experimental design for combination therapy experiment in Example 3.

Figure 5A:
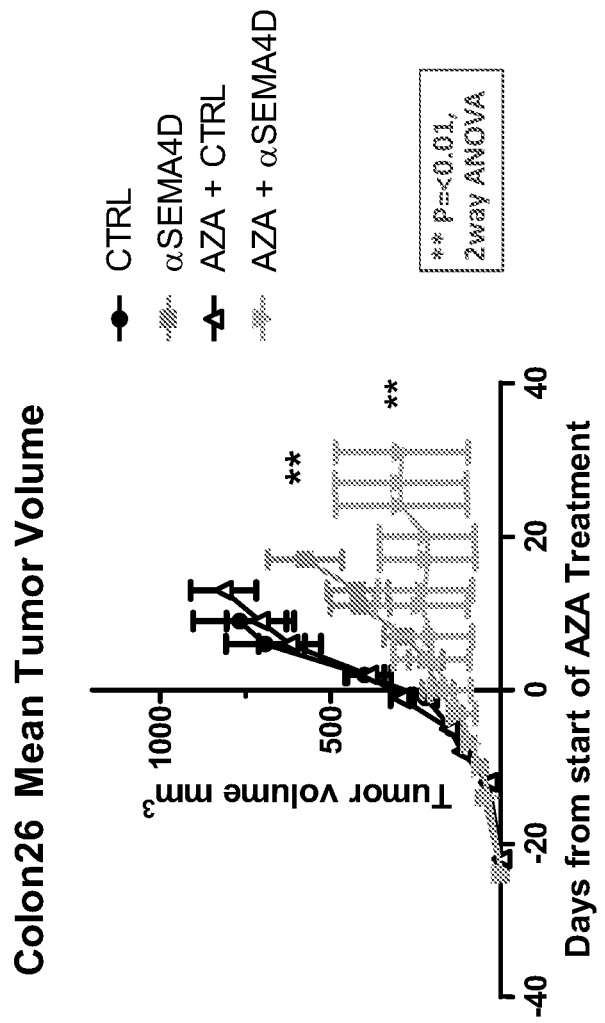
Figure 5B:
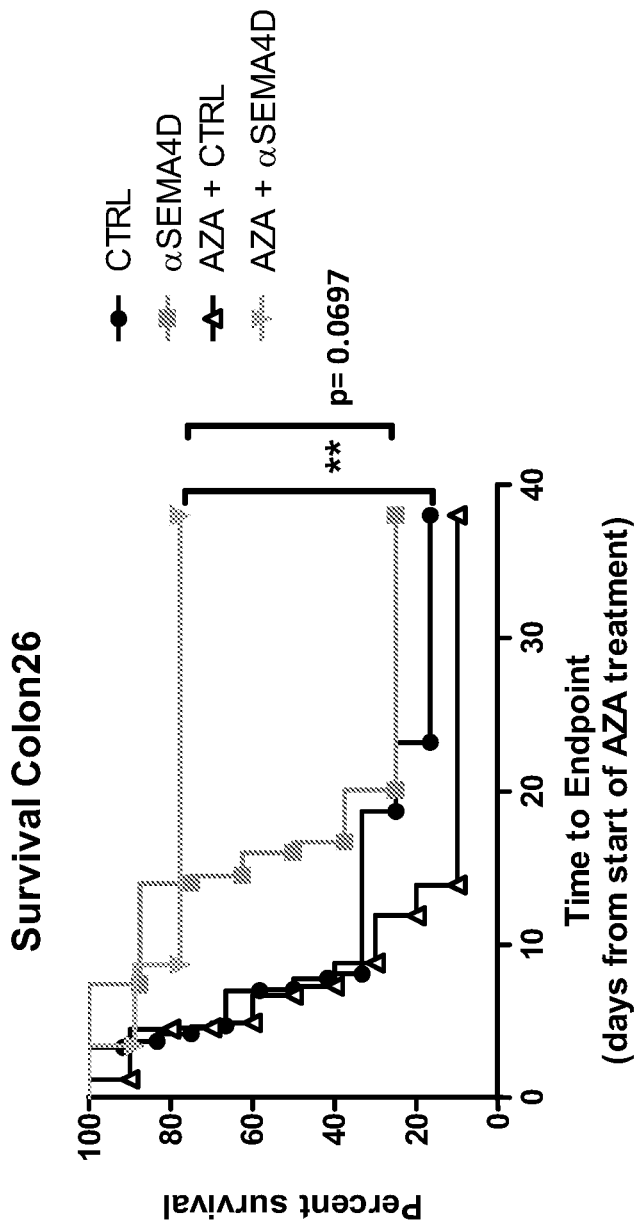

FIG. 5A shows the mean tumor volume over time for the various treatments in Example 3. Statistical significance was determined using 2-way ANOVA. $P\leq0.01$ FIG. 5B shows percent survival over time for the various treatments in Example 3. Statistical significance was determined using Mantel Cox Log Rank test. Prism reports results as non-significant at P>0.05, or very significant ("") at $P\leq0.01$.

Figure 5C:
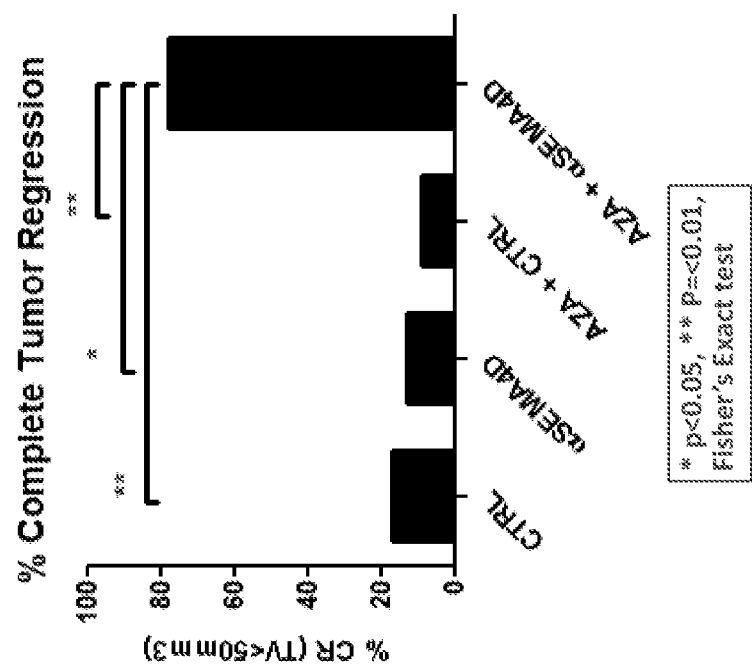

FIG. 5C is a bar graph showing the percent of complete tumor regression (tumor volume <50 mm$^3$) for the various treatments in Example 3. Statistical significance was determined using Fisher's exact test, Prism reports results as significant (symbolized by "*") at $P\leq0.05$, or very significant ("**") at $P\leq0.01$.

DETAILED DESCRIPTION

Definitions

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

As used herein, the terms "cancer" and "cancerous" refer to or describe the physiological condition in mammals in which a population of cells are characterized by unregulated cell growth. Cancers can be categorized, e.g., as solid tumors or malignancies, or hematological cancers or malignancies. Both types can migrate to remote sites as metastases. A solid tumor can be categorized, e.g., as a sarcoma, a carcinoma, a melanoma, or a metastasis thereof.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions. In certain embodiments, tumors described herein express a SEMA4D receptor, e.g., Plexin-B1, Plexin-B2, and/or CD72, and/or can express SEMA4D.

The terms "metastasis," "metastases," "metastatic," and other grammatical equivalents as used herein refer to cancer cells which spread or transfer from the site of origin (e.g., a primary tumor) to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures. The terms also refer to the process of metastasis, which includes, but is not limited to detachment of cancer cells from a primary tumor, intravasation of the tumor cells to circulation, their survival and migration to a distant site, attachment and extravasation into a new site from the circulation, and microcolonization at the distant site, and tumor growth and development at the distant site.

Examples of such solid tumors can include, e.g., squamous cell carcinoma, adenocarcinoma, basal cell carcinoma, renal cell carcinoma, ductal carcinoma of the breast, soft tissue sarcoma, osteosarcoma, melanoma, small-cell lung cancer, non-small cell lung cancer (NSCLC), adenocarcinoma of the lung, cancer of the peritoneum, hepatocellular carcinoma, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, prostate cancer, vulval cancer, thyroid cancer, head and neck cancer, any metastases thereof, or any combination thereof.

Examples of hematologic cancers or malignancies include without limitation leukemia, lymphoma, myeloma, acute myeloid leukemia, chronic myeloid leukemia, acute lymphocytic leukemia, chronic lymphocytic leukemia, hairy cell leukemia, Hodgkin lymphoma, non-Hodgkin lymphoma, multiple myeloma, any metastases thereof, or any combination thereof.

In certain embodiments, cancers that are amenable to treatment via the methods provided herein include, but are not limited to sarcomas, breast carcinomas, ovarian cancer, cervical cancer, head and neck cancer, NSCLC, esophageal cancer, gastric cancer, kidney cancer, liver cancer, bladder cancer, colorectal cancer, and pancreatic cancer. In certain embodiments cancers or tumor cells that are amenable to treatment via the methods provided herein express Plexin-B1, Plexin-B2, or CD72 receptors for SEMA4D.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to aprotein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "a non-naturally occurring polypeptide" or any grammatical variants thereof, is a conditional definition that explicitly excludes, but only excludes, those forms of the polypeptide that are, or might be, determined or interpreted by a judge or an administrative or judicial body, to be "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:.412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, the term "a non-naturally occurring polynucleotide" or any grammatical variants thereof, is a conditional definition that explicitly excludes, but only excludes, those forms of the nucleic acid or polynucleotide that are, or might be, determined or interpreted by a judge, or an administrative or judicial body, to be "naturally-occurring."

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Disclosed herein are certain binding molecules, or antigen-binding fragments, variants, or derivatives thereof. Unless specifically referring to full-sized antibodies, the term "binding molecule" encompasses full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a receptor, e.g., an epitope or an antigenic determinant. As described further herein, a binding molecule can comprise one of more "antigen binding domains" described herein. A non-limiting example of a binding molecule is an antibody or fragment thereof that retains antigen-specific binding.

As used herein, the terms "binding domain" or "antigen binding domain" refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain." Other binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable domain of a heavy chain (for camelid species) or at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and optionally includes a J chain and/or a secretory component, or an IgM antibody that includes ten or twelve complete heavy chains and ten or twelve complete light chains and optionally includes a J chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$ or $\alpha 1$-$\alpha 2$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, $IgA_2$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda ($\kappa$, $\lambda$). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant domains of the light chain (CL) and the heavy chain (CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains actually comprise the carboxy-terminus of the heavy and light chain, respectively.

As indicated above, a variable region (i.e., the "binding domain") allows the binding molecule to selectively recognize and specifically bind epitopes on antigens. That is, the VL domain and VH domain, or subset of the complementarity determining regions (CDRs), of a binding molecule, e.g., an antibody combine to form the variable region that defines a three dimensional antigen binding site. More specifically, the antigen binding site is defined by three CDRs on each of the VH and VL chains. Certain antibodies form larger structures. For example, IgA can form a molecule that includes two H2L2 units, a J chain, and a secretory component, all covalently connected via disulfide bonds, and IgM can form a pentameric or hexameric molecule that includes five or six H2L2 units and optionally a J chain covalently connected via disulfide bonds.

The six "complementarity determining regions" or "CDRs" present in an antibody antigen-binding domain are short, non-contiguous sequences of amino acids that are specifically positioned to form the binding domain as the antibody assumes its three dimensional configuration in an aqueous environment. The remainder of the amino acids in the binding domain, referred to as "framework" regions, show less inter-molecular variability. The framework regions largely adopt a n-sheet conformation and the CDRs form loops which connect, and in some cases form part of, the n-sheet structure. Thus, framework regions act to form a scaffold that provides for positioning the CDRs in correct orientation by inter-chain, non-covalent interactions. The binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5\times10^{-2}$ sec$^{-1}$, $10^{-3}$ sec$^{-1}$, $5\times10^{-3}$ sec$^{-1}$, $10^{-3}$ sec$^{-1}$, $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$, or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$, $5\times10^4$ M$^{-1}$ sec$^{-1}$, $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$, or $10^7$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of binding domains and an antigen. See, e.g., Harlow at pages 29-34. Avidity is related to both the affinity of individual binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}$ M, $10^{-2}$ M, $5\times10^{-3}$ M, $10^{-3}$ M, $5\times10^{-4}$M, $10^{-4}$M, $5\times10^{-5}$ M, $10^{-5}$ M, $5\times10^{-6}$ M, $10^{-6}$ M, $5\times10^{-7}$ M, $10^{-7}$ M, $5\times10^{-8}$M, $10^{-8}$ M, $5\times10^{-9}$M, $10^{-9}$M, $5\times10^{-10}$ M, $10^{-10}$ M, $5\times10^{-11}$M, $10^{-11}$ M, $5\times10^{-12}$M, $10^{-12}$M, $5\times10^{-13}$M, $10^{-13}$M, $5\times10^{-14}$M, $10^{-14}$M, $5\times10^{-15}$M, or $10^{-15}$M.

Antibody fragments including single-chain antibodies or other binding domains can exist alone or in combination with one or more of the following: hinge region, CH1, CH2, CH3, or CH4 domains, J chain, or secretory component. Also included are antigen-binding fragments that can include any combination of variable region(s) with one or more of a hinge region, CH1, CH2, CH3, or CH4 domains, a J chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" includes amino acid sequences derived from an immunoglobulin heavy chain, a binding molecule, e.g., an antibody comprising a heavy chain subunit includes at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, in addition to a VH domain, a CH1 domain; CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

The heavy chain subunits of a binding molecule, e.g., an antibody or fragment thereof, can include domains derived from different immunoglobulin molecules. For example, a heavy chain subunit of a polypeptide can include a CH1 domain derived from an IgG1 molecule and a hinge region derived from an IgG3 molecule. In another example, a heavy chain subunit can include a hinge region derived, in part, from an IgG1 molecule and, in part, from an IgG3 molecule. In another example, a heavy chain subunit can comprise a chimeric hinge derived, in part, from an IgG1 molecule and, in part, from an IgG4 molecule.

As used herein, the term "light chain subunit" includes amino acid sequences derived from an immunoglobulin light chain. The light chain subunit includes at least one of a VL or CL (e.g., Cκ or Cλ) domain.

Binding molecules, e.g., antibodies or antigen-binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of a typical immunoglobulin heavy chain molecule.

As used herein the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340), EU numbering system; see Kabat E A et al. op. cit. The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain. This hinge region comprises approximately 25 amino acids and is flexible, thus allowing the two N-terminal antigen binding regions to move independently.

As used herein the term "disulfide bond" includes the covalent bond formed between two sulfur atoms. The amino acid cysteine comprises a thiol group that can form a disulfide bond or bridge with a second thiol group. In certain IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody, or "bispecific antibody" refer to an antibody that has binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, *IDrugs.* 13:543-9 (2010)). A bispecific antibody can also be a diabody.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly a portion of a polypeptide that is "carboxy-terminal" or "C-terminal" to another portion of a polypeptide is that portion that comes later in the sequential polypeptide chain. For example in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "epigenetic modification(s)" refers to stably-heritable phenotype(s) resulting from chromosomal alterations without alterations to the DNA sequence. Epigenetic modifications can, in some instances lead to a disease or disorder such as cancer. Berger, S L, et al., *Genes Dev.* 23:781-783 (2009). Epigenetic modifications typically involve changes in the chromatin structure that can result in overexpression and/or repression of genes that control cellular processes such as differentiation, proliferation, and/or apoptosis. Such modifications can involve, e.g., DNA methylation and histone acetylation. See, e.g., Gnyska, A., et al., *Anticancer Res.* 33:2989-2996 (2013).

As used herein, the term "epigenetic modulating agent" refers to an agent, e.g., a therapeutic agent, which can affect, e.g., block, reduce, reverse, or alleviate, a disease-causing epigenetic modification, thereby treating the disease, e.g., cancer. Exemplary epigenetic modulating agents include DNA methyltransferase inhibitors (DNMTi) and histone deacetylase inhibitors (HDACi). A variety of HDACi and DNMTi are approved for or are being tested for treatment of certain cancers. Exemplary agents are disclosed elsewhere herein.

As used herein, the terms "histone deacetylase inhibitor(s)" or "HDAC inhibitor(s)" or "HDACi" refer to a compound or compounds that are capable of inhibiting the deacetylation of histones in vivo, in vitro, or both. HDAC inhibit the activity of at least one histone deacetylase. As a result of inhibiting the deacetylation of at least one histone, an increase in acetylated histone occurs and accumulation of acetylated histone can provide a biological marker for assessing the activity of HDAC.

As used herein, the terms "DNA methyltransferase inhibitors(s)" or "DNMT inhibitor(s)" or "DNMTi" refer to a compound or compounds that are capable of inhibiting DNA hypermethylation and/or DNA methyltransferase ("DNMT") overexpression in vivo, in vitro, or both. As a result of inhibiting DNMT overexpression and/or DNMT activity, DNMTi can, e.g., restore expression of aberrantly silenced genes such as tumor suppressor genes.

As used herein, the term "anti-SEMA4D binding molecule" refers to a molecule that specifically binds to SEMA4D, e.g., an antibody or antigen-binding fragment, variant, or derivative thereof. Unless specifically referring to full-sized antibodies such as naturally occurring antibodies, the term "anti-SEMA4D antibody" encompasses full-sized antibodies as well as antigen-binding fragments as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; retard or stop cancer cell division, reduce or retard an increase in tumor size; inhibit, e.g., suppress, retard, prevent, stop, delay, or reverse cancer cell infiltration into peripheral organs including, for example, the spread of cancer into soft tissue and bone; inhibit, e.g., suppress, retard, prevent, shrink, stop, delay, or reverse tumor metastasis; inhibit, e.g., suppress, retard, prevent, stop, delay, or reverse tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a therapy as described herein, such as an antibody, comprising one or more antigen binding domains, in combination with an epigenetic modulating agent, e.g., an HDACi, a DNMTi, and/or a combination thereof.

The term "immune modulating therapy" or "immunotherapy" refers to treatment that impacts a disease or disorder in a subject by inducing and/or enhancing an immune response in that subject. Immune modulating therapies include cancer vaccines, immunostimulatory agents, adoptive T cell or antibody therapy, and immune checkpoint blockade (Lizée et al. *Ann. Rev. Med.* 64:71-90 (2013)).

The term "immune modulating agent" refers to the active agents of immunotherapy. Immune modulating agents include a diverse array of recombinant, synthetic and natural, preparation. Examples of immune modulating agents include, but are not limited to, interleukins such as IL-2, IL-7, IL-12; cytokines such as granulocyte colony-stimulating factor (G-CSF), interferons; various chemokines such as CXCL13, CCL26, CXCL7; antagonists of immune checkpoint blockades such as anti-CTLA-4, anti-PD-1 or anti-PD-L1 (ligand of PD-1), anti-LAG3, anti-TIM3, anti-B7-H3, synthetic cytosine phosphate-guanosine (CpG) oligodeoxynucleotides, glucans; and modulators of regulatory T cells (Tregs) such as cyclophosphamide.

Target Polypeptide Description—SEMA4D

As used herein, the terms "semaphorin-4D", "SEMA4D", and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiment, SEMA4D is soluble, e.g., sSEMA4D. In another embodiment, SEMA4D can include a full-sized SEMA4D or a fragment thereof, or a SEMA4D variant polypeptide, where the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D can be proteolytically cleaved from their transmembrane form to generate 120-kDa soluble forms, giving rise to two Sema4D isoforms (Kumanogoh et al., *J. Cell Science* 116:3464 (2003)). Semaphorins consist of soluble and membrane-bound proteins that were originally defined as axonal-guidance factors which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

The SEMA4D polypeptide includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman et al., Eds. (1995) *Leucocyte Typing V* (Oxford University Press, Oxford).

SEMA4D is known to have at least three functional receptors, Plexin-B1, Plexin-B2 and CD72. Plexin-B1, is expressed in non-lymphoid tissues and has been shown to be a high affinity (1 nM) receptor for SEMA4D (Tamagnone et al., *Cell* 99:71-80 (1999)). SEMA4D stimulation of Plexin-B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to SEMA4D, Plexin-B1 signaling mediates the inactivation of R-Ras, leading to a decrease in the integrin mediated attachment to the extracellular matrix, as well as to activation of RhoA, leading to cell collapse by reorganization of the cytoskeleton (Kruger et al., *Nature Rev. Mol. Cell Biol.* 6:789-800 (2005); Pasterkamp, *TRENDS in Cell Biology* 15:61-64 (2005)). Plexin-B2 has an intermediate affinity for SEMA4D and a recent report indicates that Plexin-B2 is expressed on keratinocytes and activates SEMA4D-positive γδ T cells to contribute to epithelial repair (Witherden et al., *Immunity* 37:314-25 (2012)).

In lymphoid tissues, CD72 is utilized as a low affinity (300 nM) SEMA4D receptor (Kumanogoh et al., *Immunity* 13:621-631 (2000)). B cells and Antigen Presenting Cells (APC) express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D mouse antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs).

Cellular activation increases the surface expression of SEMA4D as well as the generation of soluble SEMA4D (sSEMA4D). The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J. Immunol.* 169:1175-1181 (2002); and Watanabe et al., *J. Immunol.* 167:4321-4328 (2001)).

Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7:1-8 (1995), each of which is herein incorporated in its entirety by reference.

The disclosure generally relates to a method of inhibiting, delaying, or reducing tumor growth or metastases in a subject, e.g., a human cancer patient, comprising administration of an antibody which specifically binds to SEMA4D, or an antigen-binding fragment, variant, or derivative thereof and an effective amount of an epigenetic modulating agent, e.g., a histone deacetylase (HDAC) inhibitor (HDACi), a DNA methyltransferase (DNMT) inhibitor (DNMTi), or any combination thereof. HDACi and DNMTi are described in detail elsewhere herein. In certain embodiments, the anti-SEMA4D antibody blocks the interaction of SEMA4D with one or more of its receptors, e.g., Plexin-B1, Plexin-B2, and/or CD72. In certain embodiments the cancer cells express Plexin-B1 and/or Plexin-B2. Anti-SEMA4D antibodies having these properties can be used in the methods provided herein. Antibodies that can be used include, but are not limited to MAbs VX15/2503, 67, 76, 2282 and antigen-binding fragments, variants, or derivatives thereof which are fully described in US 2010/0285036 A1 and US 2008/0219971 A1. Additional antibodies which can be used in the methods provided herein include the BD16 antibody described in US 2006/0233793 A1 as well as antigen-binding fragments, variants, or derivatives thereof or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit binding or activity of any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example, those described above. In a further embodiment, the binding molecule shares at least about 96%, about 97%, about 98%, about 99%, or 100% sequence identity to a reference antibody.

In certain aspects, the anti-SEMA4D antibody or antigen-binding fragment, variant, or derivative thereof can inhibit SEMA4D interaction with its receptor, e.g., Plexin-B1, Plexin-B2, or CD72. In certain aspects the anti-SEMA4D antibody or antigen-binding fragment, variant, or derivative thereof can inhibit SEMA4D-mediated Plexin-B1 signal transduction.

In certain aspects, the anti-SEMA4D antibody or antigen-binding fragment, variant, or derivative thereof competitively inhibits a reference antibody comprising a variable heavy chain region (VH) comprising the amino acid sequence SEQ ID NO: 1 and a variable light chain region (VL) comprising the amino acid sequence SEQ ID NO: 5 from binding to SEMA4D. In certain aspects, the anti-SEMA4D antibody or antigen-binding fragment, variant, or derivative thereof binds to the same SEMA4D epitope as a reference antibody comprising a VH comprising the amino acid sequence SEQ ID NO: 1 and a VL comprising the amino acid sequence SEQ ID NO: 5. In certain aspects, the VH of the anti-SEMA4D antibody or antigen-binding fragment, variant, or derivative thereof comprises three complementarity determining regions (CDRs) HCDR1, HCDR2, and HCDR3, and the VL comprises three CDRs LCDR1, LCDR2, and LCDR3, the CDRs comprising the amino acid sequences SEQ ID NO: 2, SEQ ID NO: 3, SEQ ID NO: 4, SEQ ID NO: 6, SEQ ID NO: 7, and SEQ ID NO: 8, respectively except for at least one, two, three, four, five, or six single conservative amino acid substitutions in one or more of the CDRs. In certain aspects the CDRs comprise the amino acid sequences SEQ ID NO: 2, SEQ ID NO: 3, SEQ ID NO: 4, SEQ ID NO: 6, SEQ ID NO: 7, and SEQ ID NO: 8, respectively.

In certain aspects the VH of the anti-SEMA4D antibody or antigen-binding fragment, variant, or derivative thereof comprises an amino acid sequence at least 70%, 75%, 80%, 85%, 90%, 95%, or 100% identical to SEQ ID NO: 1 and the VL of the anti-SEMA4D antibody or antigen-binding fragment, variant, or derivative thereof comprises an amino acid sequence at least 70%, 75%, 80%, 85%, 90%, 95%, or 100% identical to SEQ ID NO: 5; or the VH comprises an amino acid sequence at least 70%, 75%, 80%, 85%, 90%, 95%, or 100% identical to SEQ ID NO: 9 and the VL comprises an amino acid sequence at least 70%, 75%, 80%, 85%, 90%, 95%, or 100% identical to SEQ ID NO: 10. In certain aspects, the VH comprises the amino acid sequence SEQ ID NO: 1 and the VL comprises the amino acid sequence SEQ ID NO: 5; or the VH comprises the amino acid sequence SEQ ID NO: 9 and the VL comprises the amino acid sequence SEQ ID NO: 10.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the disclosure can be used in the methods of the present disclosure. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, Proc. Natl. Acad. Sci. USA 82:488-492 (1985); Kunkel et al., Methods Enzymol. 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In certain aspects, conservative substitutions, such as exchanging one amino acid with another having similar properties are used. Examples of conservative amino acid substitutions as taught by the PAM 250 matrix of the Dayhoff et al. model include, but are not limited to, Gly↔Ala, Val ↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. In certain aspects, mutations made in the DNA encoding the variant polypeptide maintain the reading frame and do not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., Immunity 13:633-642 (2000); Kumanogoh et al., J. Immunol. 169:1175-1181 (2002); Watanabe et al., J. Immunol. 167:4321-4328 (2001); Wang et al., Blood 97:3498-3504 (2001); and Giraudon et al., J. Immunol. 172:1246-1255 (2004), all of which are herein incorporated by reference.

Methods for measuring the anti-angiogenic ability of an anti-SEMA4D antibody or antigen-binding fragment, variant, or derivative thereof are well known in the art.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present disclosure, the parameters are set, of course, such that the percentage of identity is calculated over the full length of the reference polypeptide sequence and that gaps in homology of up to 5% of the total number of amino acids in the reference sequence are allowed.

For purposes of the present disclosure, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference anti-SEMA4D antibody (e.g., MAb VX15/2503, 67, 76, or 2282) by as few as 1 to 15 amino acid residues, as few as 1 to 10 amino acid residues, such as 6-10, as few as 5, as few as 4, 3, 2, or even 1 amino acid residue.

The constant region of an anti-SEMA4D antibody can be mutated to alter effector function in a number of ways. For example, see U.S. Pat. No. 6,737,056 B1 and U.S. Patent Application Publication No. 2004/0132101 A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant disclosure moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation.

Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to inhibit, delay, or reduce metastases in a subject, e.g., a cancer patient).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; inhibition, delay, or reduction of tumor cell growth or metastasis, binding to cell surface plexin-B1 or other receptor, or any other activity association with soluble SEMA4D or SEMA4D that is expressed on the surface of SEMA4D+ cells. In a particular embodiment, anti-SEMA4D activity includes the ability to inhibit, delay, or reduce tumor metastases, either in combination with inhibition, delay, or reduction of primary tumor cell growth and tumor metastases, or independently of primary tumor cell growth and tumor metastases. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAb BD16 were described in US Publ. No. 2008/0219971 A1, International Patent Application WO 93/14125 and Herold et al., *Int. Immunol.* 7:1-8 (1995), each of which are herein incorporated by reference in their entirety. The modifications can involve replacement of amino acid residues within the CDR such that an anti-SEMA4D antibody retains specificity for the SEMA4D antigen and has improved binding affinity and/or improved anti-SEMA4D activity.

Histone Deacetylase Inhibitors (HDACi)

As used herein, the terms "histone deacetylase inhibitor(s)," "HDAC inhibitor(s)," and "HDACi" are used interchangeably, and can refer to singular HDACi or plural HDACi.

Histone acetyl transferases (HATs) and histone deacetylases (HDACs) regulate the acetylation status of histones. Histone acetyl transferases are enzymes that acetylate the lysine residues in core histones resulting in less compact and more transcriptionally active chromatin, which leads to gene expression. HDACs, conversely, are enzymes that catalyze the removal of acetyl groups from lysine residues in the amino terminal tails of the nucleosomal core histones. HDACs can be divided into three classes based on structural homology. Class I HDACs (HDACs 1, 2, 3, and 8) are related to the yeast RPD3 gene. Class IIA (HDACs 4, 5, 7, and 9) bear similarity to the yeast Hda1 gene. Class III, also known as sirtuins, are related to the Sir2 gene and include SIRT1-7. Class IV, which only contains HDAC11, shares features of both Class I and II. See, e.g., Mottamal, M., et al., *Molecules* 20:3898-3941 (2015).

Certain HDAC inhibitors act by binding to the zinc-containing catalytic domain of the HDACs. These can be classified based on the chemical moiety that binds to the zinc ion, or as cyclic tetrapeptides, which bind to the zinc ion with a thiol group. See, e.g., Drummond, D. C., et al., *Ann. Rev. Pharmacol. Toxicol.* 45:495-528 (2005). These include, without limitation: hydroxamic acids (or hydroxamates), such as trichostatin A; cyclic tetrapeptides (such as trapoxin B) and the depsipeptides; benzamides; electrophilic ketones; and aliphatic acid compounds (short-chain fatty acids (SCFAs) such as phenylbutyrate and valproic acid. See, e.g., Porcu, M., and Chiarugi, A., *Trends Pharmacolog. Sci.* 26:94-103 (2005). More specifically, HDAC inhibitors include, without limitation, hydroxamic acids Vorinostat (SAHA), Belinostat (PXD101), LAQ824, and Panobinostat (LBH589); and the benzamides: entinostat (MS-275), CI994, and Mocetinostat (MGCD0103). The sirtuin Class III HDACs are dependent on NAD+ and are, therefore, inhibited by nicotinamide, as well as derivatives of NAD, dihydrocoumarin, naphthopyranone, and 2-hydroxynaphthaldehydes. Id.

Non-limiting examples of HDAC inhibitors for use in inhibiting histone deacetylase, inducing terminal differentiation, cell growth arrest and/or apoptosis in malignant cells, and/or inducing differentiation, cell growth arrest, and/or apoptosis of tumor cells in a tumor are listed in Table 2. It is understood that the HDAC inhibitors include any salts, crystal structures, amorphous structures, hydrates, derivatives, metabolites, stereoisomers, structural isomers and prodrugs of the HDAC inhibitors described herein.

TABLE 2

Non-limiting list of HDAC inhibitors

| Name | Structure | Reference |
| --- | --- | --- |
| Entinostat | 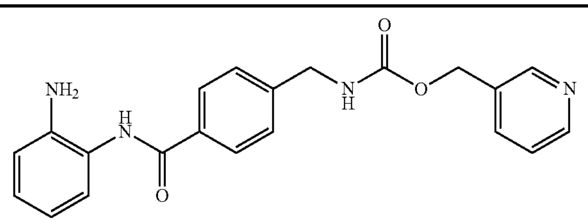 | Bracker, et al. Int J Oncol. 35:909-20 (2009). |
| Vorinostat | 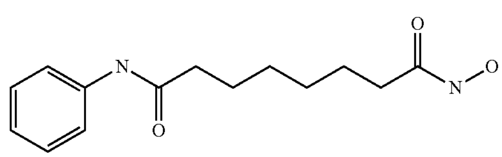 [SMILES: O=C(CCCCCCC(=O)Nc1ccccc1)NO] | Lee, J.-H:,et al.. Proc. Natl. Acad. Sci. USA 110: 15704-9 (2013). |
| Romidepsin | 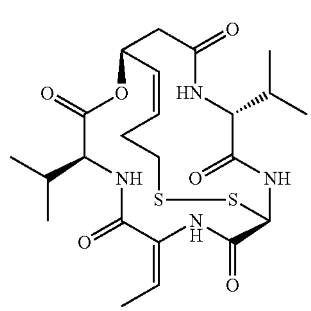 [SMILES: C/C=C1/NC(=O)[C@@H]2NC(=O)[C@@H](C(C)C)NC(=O)C[C@@H](/C=C\CCSS2)OC(=O)[C@H](C(C)C)NC1=O] | Nakajima H, et al., Exp. Cell Res. 241A26-33 (1998). |

TABLE 2-continued

Non-limiting list of HDAC inhibitors

| Name | Structure | Reference |
| --- | --- | --- |
| Chidamide | 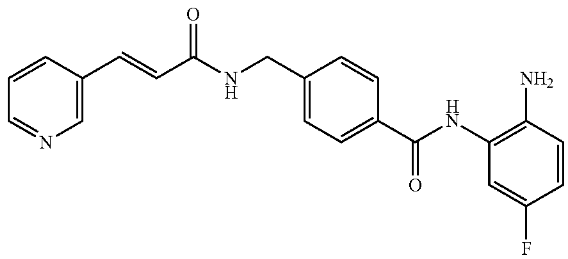 [SMILES: Nc1ccc(F)cc1NC(=O)c1ccc(CNC(=O)/C=C/c2cccnc2)cc1] | Qiao, Z et al., Biochem Biophys Res Commun. 434:95-101 (2013). |
| Panobinostat | 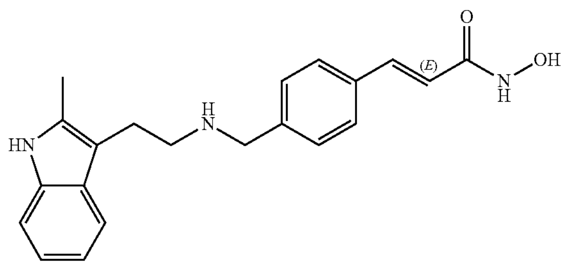 [SMILES: Cc1[nH]c2ccccc2c1CCNCc1ccc(/C=C/C(=O)NO)cc1] | Prince, HM; and M Bishton Hematology Meeting Reports. Parkville, Australia: Peter MacCallum Cancer Centre and Univ. of Melbourne. 3 (1): 33-38 (2009). |
| Belinostat | 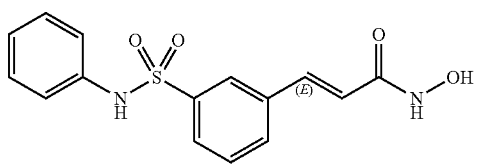 [SMILES: O=C(/C=C/c1cccc(S(=O)(=O)Nc2ccccc2)c1)NO] | Plumb JA, et al. Mol Cancer Ther 2:721-728 (2003). |
| Valproic Acid | 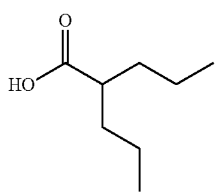 | Phiel et al. J. Biol. Chem. 276:36734-36741 (2001); Gottlicher et al. EMBO J 20:6969-6978 (2001). |
| Mocetinostat | 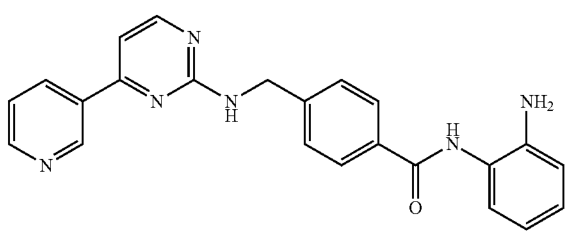 [SMILES: Nc1ccccc1NC(=O)c1ccc(CNc2nccc(-c3cccnc3)n2)cc1] | Fournel et al. Mol. Cancer Ther. 7:759-768 (2008). |
| Abexinostat | 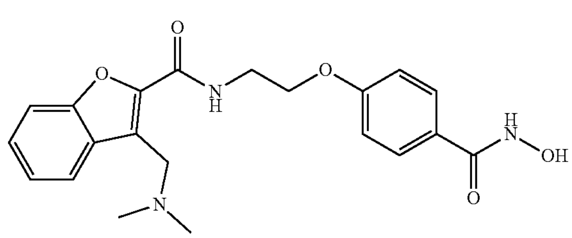 [SMILES: CN(C)Cc1c(C(=O)NCCOc2ccc(C(=O)NO)cc2)oc2ccccc12] | Buggy, JJ, et al., Mol. Cancer Ther. 5:1309-1317 (2006). |

TABLE 2-continued

Non-limiting list of HDAC inhibitors

| Name | Structure | Reference |
| --- | --- | --- |
| Pracinostat | 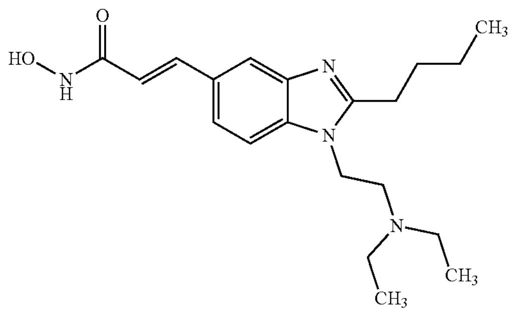 [SMILES: CCCCc1nc2cc(/C=C/C(=O)NO)ccc2n1CCN(CC)CC] | Novotny-Diermayr; V., et al. Mol Cancer Ther. doi:10.1158/1535-7163.MCT-09-0689 (2010). |
| Resminostat | 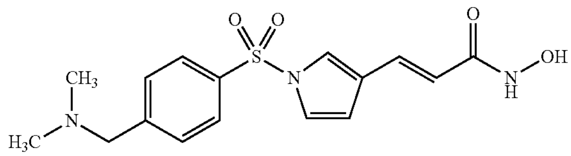 [SMILES: CN(C)Cc1ccc(S(=O)(=O)n2ccc(/C=C/C(=O)NO)c2)cc1] | Mandi-Weber S, et al., Br. J. Haematol. 149:518-528 (2010). |
| Givinostat | 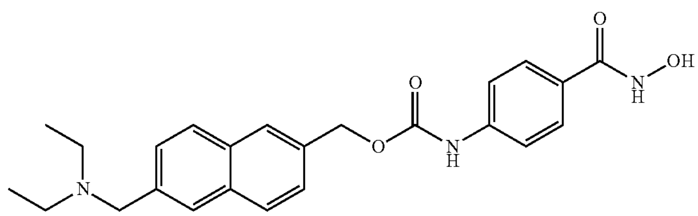 [SMILES: CCN(CC)Cc1ccc2cc(COC(=O)Nc3ccc(C(=O)NO)cc3)ccc2c1] | Leoni F, and Fossati G. Mol. Med. 11:1 (2005). |
| Quisinostat | 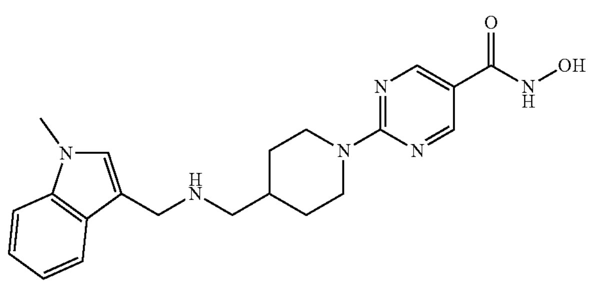 [SMILES: Cn1cc(CNCC2CCN(c3ncc(C(=O)NO)cn3)CC2)c2ccccc21] | Arts. J et al., Clin. Cancer Res. 15:6841-51 (2009). |
| Kevetrin | 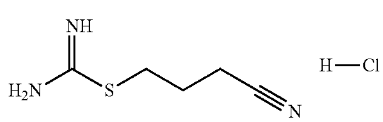 | clinicaltrials.gov /ct2/show/ NCT01664000?term= kevetrin&rank=1. |
| CUDC-101 (Curis) | 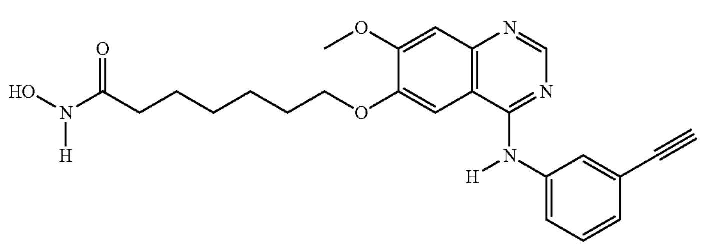 [SMILES: C#Cc1cccc(Nc2ncnc3cc(OC)c(OCCCCCCC(=O)NO)cc23)c1] | Lai, et al., Cancer Res. 70:3647-3656 (2010). |

TABLE 2-continued
Non-limiting list of HDAC inhibitors
| Name | Structure | Reference |
|---|---|---|
| 4SC-202 | 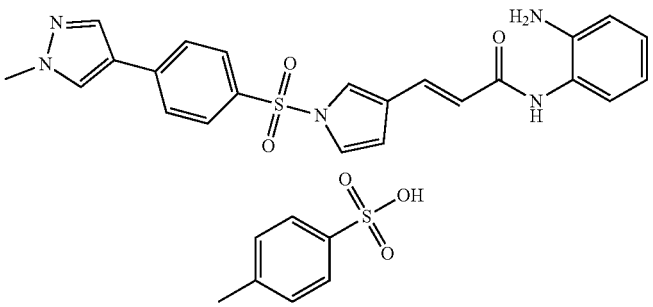 | Zhijun, H., et al., Tumor Biol. 37:10257 (2016). |
| ACY-241 | 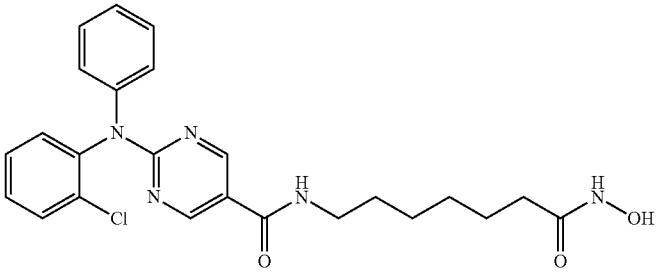 [SMILES: O=C(CCCCCCNC(=O)c1cnc(N(c2ccccc2)c2ccccc2Cl)nc1)NO] | Niesvizky et al. Blood 126:3040 (2015). |
| AR-42 | 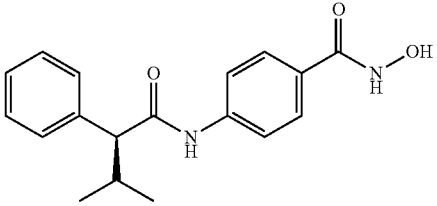 [SMILES: CC(C)[C@H](C(=O)Nc1ccc(C(=O)NO)cc1)c1ccccc1] | Lin TY et al., Blood 115:4217-4225 (2010); Sargeant AM et al., Cancer Res. 68:3999-4009 (2008). |
| Tefinostat | 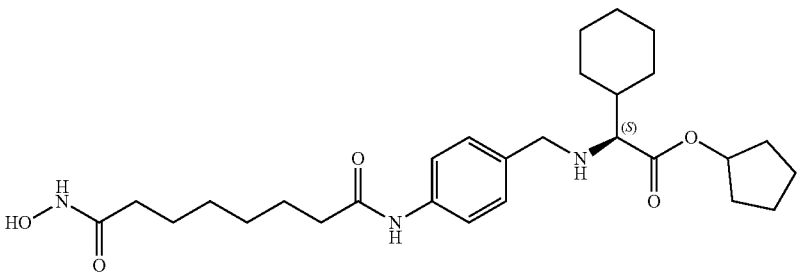 | Zabkiewicz, J., et al., Blood 122:1297 (2013). |
| CHR-3996 | 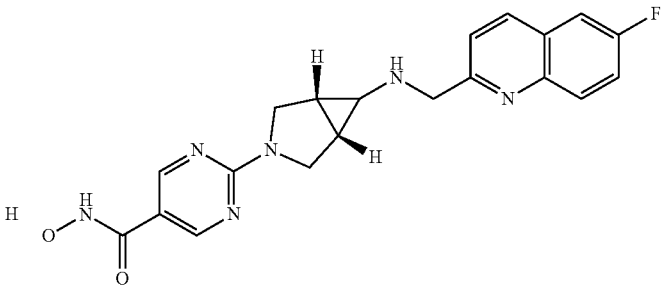 | Moffat, D., et al. J. Med. Chem. 53:8663-78 (2010). |

TABLE 2-continued

Non-limiting list of HDAC inhibitors

| Name | Structure | Reference |
|---|---|---|
| Ricolinostat (ACY-1215) | 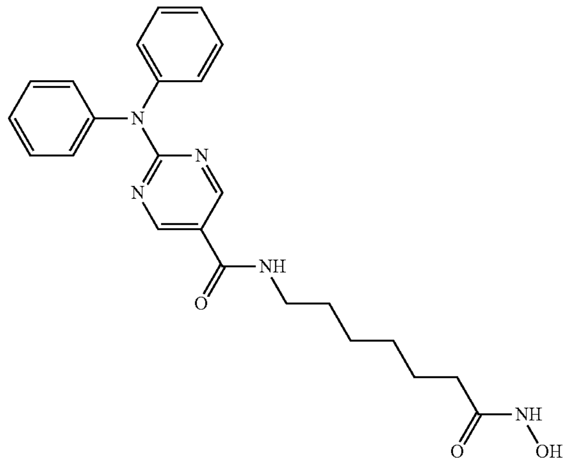 [SMILES: O=C(CCCCCCNC(=O)c1cnc(N(c2ccccc2)c2ccccc2)nc1)NO] | Yee AJ et al., Blood 126:3055 (2015); Santo L., et al., Blood. 119:2579-89 (2012). |
| CG200745 | 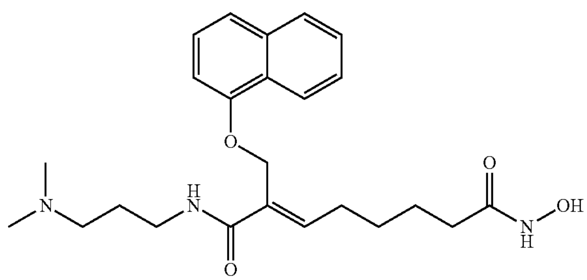 [SMILES: CN(C)CCCNC(=O)/C(=C/CCCCC(=O)NO)COc1cccc2ccccc12] | Chun SM, et al., PLoS One. 10:e0119379. doi:10.1371/journal. pone.0119379. eCollection 2015. |

In certain embodiments, HDAC inhibitors useful in the methods provided herein include Entinostat, Vorinostat, Romidepsin, Chidamide, Panobinostat, Belinostat, Valproic acid, Mocetinostat, Abexinostat, Pracinostat, Resminostat, Givinostat, Quisinostat, Kevetrin, CUDC-101, 4SC-202, ACY-241, AR-42, Tefinostat, CHR-3996, Ricolinostat (ACY-1215), and/or CD200745. Some FDA approved HDAC inhibitors for cancer treatment, as well as HDAC inhibitors that are currently in pending or completed clinical trials, are listed below.

Food and Drug Administration (FDA) Approved HDAC Inhibitors. Vorinostat was licensed by the U.S. FDA in October 2006 for the treatment of cutaneous T cell lymphoma (CTCL). Romidepsin (trade name Istodax) was licensed by the US FDA in November 2009 for cutaneous T-cell lymphoma (CTCL). Chidamide was approved by China in 2015 for peripheral T-cell lymphoma (PTCL). Panobinostat (trade name Farydak) was licensed by the US FDA in February 2015 for the treatment of multiple myeloma. Belinostat (PXD101) was licensed by the FDA for the treatment of peripheral T-cell lymphoma in 2014.

In one non-limiting aspect, the HDAC inhibitor is Entinostat (ENT). Entinostat has the IUPAC chemical name pyridin-3-ylmethyl N-[[4-[(2-aminophenyl)carbamoyl]phenyl]methyl] carbamate. ENT, also known as SNDX-275 and MS-275, is an inhibitor of class I HDACs (Syndax Pharmaceuticals). ENT is a benzamide histone deacetylase inhibitor that inhibits HDAC1 and HDAC3 with IC50 of 0.51 µM and 1.7 µM. ENT is currently undergoing clinical trials for treatment of various cancers.

DNA Methyltransferase Inhibitors

As used herein, the terms "DNA methyltransferase inhibitor(s)," "DNMT inhibitor(s)," and "DNMTi" are used interchangeably, and can refer to singular DNMTi or plural DNMTi.

DNA methyltransferases catalyze the addition of methyl groups to the 5' carbon of cytosine residues. In cancer cells, silencing of tumor suppressor genes occurs though DNMT-mediated methylation. Gravina et al., *Molecular Cancer* 9:305-320 (2010). Several isoforms of DNMTs exist, including DNMT1, DNMT-3a and DNMT-3b. Id. A variety of DNMTi have been identified, and two are approved for cancer therapy in the United States. The classes of molecules include nucleoside analogs, antisense oligonucleotides, small molecule enzyme inhibitors, and agents that block the interaction of DNMTs with DNA.

Non-limiting examples of DNMTi for use in inhibiting DNA methyltransferases, inducing terminal differentiation, cell growth arrest and/or apoptosis in malignant cells, and/or inducing differentiation, cell growth arrest, and/or apoptosis of tumor cells in a tumor are listed in Table 3. It is understood that the DNMTi include any salts, crystal structures, amorphous structures, hydrates, derivatives, metabolites, stereoisomers, structural isomers and prodrugs of the DNMT inhibitors described herein.

TABLE 3

Non-limiting list of DNMT inhibitors

| Name and Synonyms | Structure | Reference |
|---|---|---|
| Azacytidine (trade name VIDAZA ®); 5-azacytidine; Azacytidine; 320-67-2; Ladakamycin; 4-Amino-1-beta-D-ribofuranosyl-s-triazin-2(1H)-one; U-18496 | (structure) | Cihák A., Oncology 30:405-422 (1974) |
| Decitabine (trade name: DACOGEN ®); 5-aza-2'-deoxycytidine; 5-aza-dCyd; Deoxyazacytidine; dezocitidine; 4-amino-1-[(2R,4S,5R)-4-hydroxy-5-(hydroxymethyl)oxolan-2-yl]-1,3,5-triazin-2-one | (structure) | Kantarjian H., et al., Cancer 106:1794-1803 (2006) |
| Zebularine; 1-(β-D-Ribofuranosyl)-2(1H)-pyrimidinone; Pyrimidin-2-one β-D-ribofuranoside; 1-[(2R,3R,4S,5R)-3,4-dihydroxy-5-(hydroxymethyl)oxolan-2-yl]pyrimidin-2-one | (structure) | Zhou, L., et al., J. Mol. Biol. 321:591-599 (2002) |
| SGI-110; 2'-Deoxy-5'-O-[(2'-deoxy-5-azacytidin-3'-O-yl)(hydroxy)phosphoryl] guanosine sodium salt; guadecitabine sodium | (structure) | Lavelle, D., et al., J. Transl. Med. 8:92 (2010) |
| Epigallocatechin gallate; (-)-epigallocatechin-3-gallate; EGCG | (structure) | Fang, MZ., et al., Cancer Res. 63:7563-7570 (2003); Li, Y. and Tollefsbol, TO., Curr. Med. Chem 17:2141-2151 (2010) |
| MG98 | 2'O-CH3—substituted phosphorothioate oligodeoxynucleotide antisense molecule designed to hybridize to the 3' untranslated region of the human DNMT1 mRNA. | Klisovic, TB., et al., Clin. Cancer Res. 14:2444-2449 (2008) |

TABLE 3-continued

Non-limiting list of DNMT inhibitors

| Name and Synonyms | Structure | Reference |
|---|---|---|
| RG108; N-Phthalyl-L-tryptophan; 2-(1,3-dioxo-1,3-dihydro-2H-isoindol-2-yl)-3-(1H-indol-3-yl)propanoic acid | 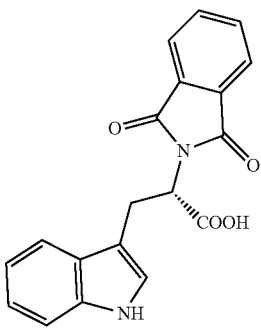 [SMILES: O=C(O)[C@H](Cc1c[nH]c2ccccc12)N1C(=O)c2ccccc2C1=O] | Brueckner, B., et al., Cancer Res. 65:6305-6311 (2005) |
| Procainamide; 4-amino-N-2-(diethylamino)ethyl-benzamide | 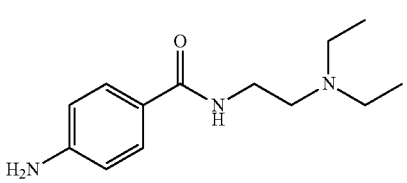 [SMILES: CCN(CC)CCNC(=O)c1ccc(N)cc1] | Lee, BH., et al.,J Biol. Chem. 280:40749-40756 (2007) |
| Hydralazine; phthalazin-1-ylhydrazine; | 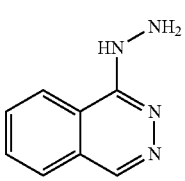 [SMILES: NNc1nncc2ccccc12] | Zambrano, P., et al., BMC Cancer 5:44 (2005) |

In certain embodiments, DNMT inhibitors useful in the methods provided herein include azacytidine, decitabine, zebularine, SGI-110, epigallocatechin gallate, MG98, RG108, procainamide, and/or hydralazine. Some FDA approved DNMT inhibitors for cancer treatment, as well as DNMT inhibitors that are currently in pending or completed clinical trials, are listed below.

Food and Drug Administration (FDA) Approved and in trial DNMTi. Azacytidine, marketed as VIDAZA®, was approved by the FDA for treatment of myelodysplastic syndrome (MDS) on May 19, 2004, and is in clinical trials for advanced solid tumors. Azacytidine has been shown to enhance activity of immune checkpoint inhibitors (ICP) in preclinical melanoma and colon cancer models by upregulating the interferon (IFN) pathway and by de-repressing viral antigens, thereby making the tumor more immunogenic and susceptible to effective ICP therapy. (Li et al., Oncotarget 5:587 (2014) and Roulois et al., Cell 162:961 (2015)). Azacytidine was further shown to upregulate expression of cancer testes antigens (CTA) in tumors leading to increased T cell activity against CTA in patients with MDS, acute myeloid leukemia (AML), and chronic myelomonocytic leukemia (CMML) (Gang, A O. et al. Blood Cancer J. doi:10.1038/bcj.2014.14. (2014)). Juergens, R A. et al., (Cancer Discov. 1:598-607 (2011)) used azacytidine and entinostat in refractory advanced NSCLC. Six patients from this trial were enrolled in an additional trial (Wrangle, J., et al., Oncotarget 4:2067-2079 (2013)) with immune checkpoint inhibitors, with five patients developing responses. See also: blogs.biomedcentral.com/on-biology/2015/03/26/improving-lung-cancer-immunotherapy-using-epigenetic-approaches/(visited Mar. 16, 2017).

Decitabine, marketed as DACOGEN®, is approved for the treatment of MDS, and is also approved in Europe for the treatment of AML and is in clinical trials for AML. SGI-110 is in phase II clinical trials for the treatment of AML. MG98 completed phase I clinical trials for advanced solid tumors. ECGC completed phase II clinical trials for prostate cancer.

In one non-limiting aspect the DNMTi is Azacytidine. Azacytidine is a chemical analog of the nucleoside cytosine. Azacytidine can, among other activities, incorporate into DNA causing hypomethylation of DNA through covalent binding with DNMT, preventing DNA synthesis and leading to cytotoxicity and degradation of the trapped DNMT. Stresemann, C., and Lyko, F., Int. J Cancer 123:8-13 (2008). Treatment Methods Using Therapeutic Anti-SEMA4D Binding Molecules and Epigenetic Modulating Agent, e.g., an HDACi and/or a DNMTi This disclosure provides a method for inhibiting, delaying, or reducing malignant cell growth in a subject with cancer by administering to the subject a combination therapy comprising an effective amount of an isolated binding molecule that specifically binds to SEMA4D, e.g., an anti-SEMA4D antibody or antigen-binding fragment, variant, or derivative thereof, in combination with an effective amount of an epigenetic modulating agent, e.g., an HDACi, a DNMTi, and/or a combination thereof. Exemplary anti-SEMA4D antibodies and exemplary epigenetic modulating agents are described in detail elsewhere herein. In certain aspects, administration of the combination therapy provided herein can inhibit tumor or malignant cell growth partially or completely, can delay the progression of tumor and malignant cell growth in the subject, can prevent metastatic spread in the subject, can reduce the subject's tumor size, e.g., to allow more successful surgical removal, can decrease tumor vasculature in the subject, or can result in any combination of positive therapeutic responses in the subject. Exemplary therapeutic responses that can be achieved are described herein.

In certain aspect, administration of the combination therapy can result in enhanced therapeutic efficacy relative to administration of the anti-SEMA4D antibody or fragment thereof or the epigenetic modulating agent alone. In certain aspects the improved treatment efficacy is synergistic, and is greater than the additive efficacy of each individual agent. In certain aspects the improved treatment efficacy over either agent administered alone, measured, e.g., in increased tumor growth delay (TGD), increased frequency of tumor regression, e.g., complete tumor regression, or increased survival is at least 5%, at least 10%, at least 20%, at least 5%, at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, or at least 1000%. In certain aspects the improved treatment efficacy over the additive efficacy of both agents administered individually, measured, e.g., in increased tumor growth delay (TGD), increased frequency of tumor regression, e.g., complete tumor regression, or increased survival is at least 5%, at least 10%, at least 20%, at least 5%, at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, or at least 1000%.

In certain aspects, the anti-SEMA4D antibody or fragment can be VX15/2503, mAb 67, or an antigen-binding fragment, variant or derivative thereof. For example the antibody or fragment thereof can include a variable heavy chain (VH) comprising VH CDRs 1-3 comprising SEQ ID NOS: 2, 3, and 4, respectively, and a variable light chain (VL) comprising VL CDRs 1-3 comprising SEQ ID NOS: 6, 7, and 8, respectively, or the VH and VL comprise, respectively, SEQ ID NO: 1 and SEQ ID NO: 5, or SEQ ID NO: 9 and SEQ ID NO: 10.

In certain aspects the method provided herein comprises administration of an anti-SEMA4D antibody or antigen-binding fragment, variant, or derivative thereof and an HDACi that inhibits an HDAC that can be a Class I, Class IIA, Class IIB, Class IV HDAC, and/or any combination thereof, e.g., an HDAC comprises a zinc-containing catalytic domain. In certain aspects, the HDACi can include a moiety that binds to the zinc-containing catalytic domain of the HDAC. For example, in certain aspects, the HDACi can include one or more, or a combination of chemical moieties such as, but not limited to, a hydroxamic acid or a salt thereof, a cyclic tetrapeptide, a depsipeptide, a benzamide, an electrophilic ketone, and/or an aliphatic acid or a salt thereof. Non-limiting examples of HDACi that can be used in the treatment method provided herein include Vorinostat, Romidepsin, Chidamide, Panobinostat, Belinostat, Valproic acid or a salt thereof, Mocetinostat, Abexinostat, Entinostat, Pracinostat, Resminostat, Givinostat, Quisinostat, Kevetrin, CUDC-101, AR-42, Tefinostat (CHR-2845), CHR-3996, 4SC-202, CG200745, ACY-1215, ACY-241, and/or any combination thereof. In certain aspects, the HDACi can be Entinostat (Pyridin-3-ylmethyl N-[[4-[(2-aminophenyl)carbamoyl]phenyl]methyl]carbamate).

In certain aspects the method provided herein comprises administration of an anti-SEMA4D antibody or antigen-binding fragment, variant, or derivative thereof and a DNMTi that inhibits DNMT1, DNMT-3a, DNMT-3b, and/or any combination thereof. For example, in certain aspects, the DNMTi can include one or more, or a combination of chemical moieties such as, but not limited to, azacytidine, decitabine, zebularine, SGI-110, epigallocatechin gallate, MG98, RG108, procainamide, hydralazine, and/or any combination thereof. In certain aspects, the DNMTi can be azacytidine.

According to the method provided herein, the anti-SEMA4D binding molecule, e.g., antibody or antigen-binding fragment, variant, or derivative thereof, and the epigenetic modulating agent, e.g., the HDACi, the DNMTi, or any combination thereof can be administered separately or simultaneously. Either agent can be administered before the other or the agents can be administered simultaneously, e.g., in a single formulation. Moreover, the routes of dosing, formulation of the agents, and/or schedules of dosing can be the same or different.

According to the method provided herein, the anti-SEMA4D binding molecule, e.g., the antibody or antigen-binding fragment, variant, or derivative thereof that specifically binds to SEMA4D, and the epigenetic modulating agent, e.g., the HDACi, the DNMTi, and/or any combination thereof are administered to a subject with cancer. The subject's cancer can be newly diagnosed, or in certain aspects, the administration can follow more traditional cancer treatments. In certain aspects, administration of the combination therapy provided herein can be used as a preventative measure in a subject with high susceptibility to develop a certain cancer, or to prevent recurrence of a cancer that has been previously treated. The subject's cancer can be, e.g., a solid tumor, a hematological malignancy, any metastasis thereof, or any combination thereof.

In certain aspects, the subject's cancer is a solid tumor or metastasis thereof. The solid tumor can be, e.g., a sarcoma, a carcinoma, a melanoma, any metastases thereof, or any combination thereof. Examples of solid tumors that can be treated according to the method provided herein include, without limitation, squamous cell carcinoma, adenocarcinoma, basal cell carcinoma, renal cell carcinoma, ductal carcinoma of the breast, soft tissue sarcoma, osteosarcoma, melanoma, small-cell lung cancer, non-small cell lung cancer, adenocarcinoma of the lung, cancer of the peritoneum, hepatocellular carcinoma, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, any metastases thereof, or any combination thereof.

In certain aspects, the cancer is a hematologic malignancy or metastasis thereof. Examples of hematologic malignancies that can be treated according to the method provided herein include, without limitation, leukemia, lymphoma, myeloma, acute myeloid leukemia, chronic myeloid leukemia, acute lymphocytic leukemia, chronic lymphocytic leukemia, hairy cell leukemia, Hodgkin lymphoma, non-Hodgkin lymphoma, multiple myeloma, any metastases thereof, or any combination thereof.

In certain aspects, the cancer treatment method provided herein can further include administration of an additional cancer therapy. The additional cancer therapy can take place simultaneously with the administration of combination therapy provided herein, before the combination therapy provided herein, or after the combination therapy provided herein. In certain aspects the additional therapy can include, without limitation, surgery, chemotherapy, radiation therapy, administration of a cancer vaccine, administration of an immunostimulatory agent, adoptive T cell or antibody therapy, administration of an immune checkpoint blockade inhibitor, administration of a regulatory T cell (Treg) modulator, or a combination of such therapies.

Administration of the epigenetic modulating agent, e.g., the HDACi, the DNMTi, and/or any combination thereof, in combination with the anti-SEMA4D binding molecule, e.g., an antibody or antigen-binding fragment, variant, or derivative thereof can be useful for the treatment of various malignant and non-malignant tumors. By "anti-tumor activity" is intended a reduction in the rate of malignant cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. "Anti-tumor activity" can also comprise promotion of immune infiltration into the tumor, a shift toward functional, tumor-specific, IFNγ-secreting CD8$^+$ cytotoxic T cells, an increase in the ratio of T effector cells to T regulatory cells, increased T-cell activity, infiltration and activation of antigen presenting cells that cross-present tumor antigens and locally activate tumor-specific T cells, reduced tumor-associated angiogenesis, inhibition of tumor progression, and enhanced survival. For example, therapy with an epigenetic modulating agent, e.g., an HDACi, a DNMTi, and/or a combination thereof and an anti-SEMA4D antibody can elicit a physiological response, for example, inhibition, delay or reduction of tumor or malignant cell growth and metastases, which is beneficial with respect to treatment of cancer associated with SEMA4D-expressing cells in a human.

In certain aspects, combination therapy with an epigenetic modulating agent, e.g., an HDACi, a DNMTi, and/or a combination thereof, and an anti-SEMA4D binding molecule, e.g., an antibody or fragment thereof, can be used as a medicament, in particular for use in the treatment or prophylaxis of cancer or for use in a precancerous condition or lesion. In certain aspects, combination therapy with an epigenetic modulating agent, e.g., an HDACi, a DNMTi, and/or a combination thereof, and an anti-SEMA4D binding molecule, e.g., an antibody or fragment thereof, can be used for the treatment of a SEMA4D over-expressing cancer, or cancer associated with SEMA4D-expressing cells.

In accordance with the treatment methods provided herein, administration of an epigenetic modulating agent, e.g., an HDACi, a DNMTi, and/or a combination thereof, and an anti-SEMA4D binding molecule, e.g., an antibody or antigen binding fragment, variant, or derivative thereof, as defined elsewhere herein can be used to promote a positive therapeutic response in the subject with cancer or predisposed to contract cancer. A "positive therapeutic response" with respect to cancer is intended to include an improvement in the disease in association with the "anti-tumor" activity is intended a reduction in the rate of malignant cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such positive therapeutic responses are not limited to the route of administration. The methods provided herein can be drawn to inhibiting, delaying, or reducing tumor growth, malignant cell growth, and metastases in a subject with cancer. Thus, as a non-limiting example, an improvement in the disease can be characterized as a reduction in tumor growth or absence of tumors. As described elsewhere herein, the therapeutic response achieved upon administration of the provided combination therapy can be greater than the corresponding therapeutic response achieved upon administering an epigenetic modulating agent or anti-SEMA4D binding molecule individually. In certain aspects the therapeutic response achieved is greater than the additive response expected upon administration of the two agents. In other words, the therapeutic response achieved is synergistic. In certain aspects, the synergistic response can result in a more effective treatment, a faster treatment, or can allow treatment with reduced dosages of the agents in the combination therapy.

Pharmaceutical Compositions and Administration Methods

This disclosure provides a composition, e.g., a pharmaceutical composition, which includes an effective amount of an anti-SEMA4D binding molecule, e.g., an antibody, or antigen-binding fragment, variant, or derivative thereof, and an effective amount of an epigenetic modulating agent, e.g., an HDACi, a DNMTi, and/or a combination thereof. The composition can further comprise one or more pharmaceutically acceptable carriers or excipients, and/or one or more additional therapeutic agents, examples of which are disclosed elsewhere herein. Suitable anti-SEMA4D binding molecules and epigenetic modulating agents for use in such a pharmaceutical composition are provided herein.

In certain aspects the pharmaceutical composition includes an effective amount of an anti-SEMA4D antibody or antigen-binding fragment thereof that includes a VH and a VL, where the VH and VL comprises the CDR amino acid sequences contained in MAbs VX15/2503 and in MAb 67, namely, an HCDR1 comprising the amino acid sequence SEQ ID NO: 2, an HCDR2 comprising the amino acid sequence SEQ ID NO: 3, an HCDR3 comprising the amino acid sequence SEQ ID NO: 4, an LCDR1 comprising the amino acid sequence SEQ ID NO: 6, an LCDR2 comprising the amino acid sequence SEQ ID NO: 7, and an LCDR3 comprising the amino acid sequence SEQ ID NO: 8. In certain aspects the pharmaceutical composition includes an effective amount of an anti-SEMA4D antibody or antigen-binding fragment thereof that includes the VH and VL amino acid sequences of MAb VX15/2503, namely, a VH comprising the amino acid sequence SEQ ID NO: 1 and a VL comprising the amino acid sequence SEQ ID NO: 5.

In certain aspects the pharmaceutical composition includes an effective amount of the HDACi entinostat. In certain aspect the pharmaceutical composition includes an effective amount of the DNMTi azacytidine.

An exemplary pharmaceutical composition provided herein includes an effective amount of MAb VX15/2503 and an effective amount of entinostat. Another exemplary pharmaceutical composition provided herein includes an effective amount of MAb VX15/2503 and an effective amount of azacytidine. In certain aspects the "effective amount" of a particular agent included in the provided pharmaceutical composition can be different, e.g., lower, than the amount of the agent that would be effective as an individual therapy. In certain aspects, the therapeutic efficacy of the pharmaceutical composition provided herein is greater than the additive effect of the included agents were they to be administered individually.

The route of administration of the epigenetic modulating agent in combination with the anti-SEMA4D binding molecule, e.g., antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. The modes of administration of the two agents can be the same or different. While all these forms of administration are clearly contemplated as being within the scope of the methods provided herein, a non-limiting example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, the epigenetic modulating agent and/or the anti-SEMA4D binding molecule, e.g., the antibody, or antigen-binding fragment, variant, or derivative thereof can be delivered directly to the site of the adverse cellular population thereby increasing the exposure of the diseased tissue to the therapeutic agent.

Methods of preparing and administering the combination therapy provided herein that includes the epigenetic modulating agent, e.g., an HDACi, a DNMTi, and/or a combination thereof in combination with the anti-SEMA4D binding molecule, e.g., the antibody, or antigen-binding fragment, variant, or derivative thereof, to a subject in need thereof are well known to or are readily determined by those skilled in the art.

As discussed herein, the epigenetic modulating agent, e.g., an HDACi, a DNMTi, and/or a combination thereof in combination with the anti-SEMA4D binding molecule, e.g., an antibody, or antigen-binding fragment, variant, or derivative thereof can be administered in a pharmaceutically effective amount for the in vivo treatment of cancer. In this regard, it will be appreciated that the disclosed epigenetic modulating agent and binding molecule can be formulated so as to facilitate administration and promote stability of the active agent. In certain embodiments, pharmaceutical compositions in accordance with the methods provided herein comprise a pharmaceutically acceptable, non-toxic, sterile carrier such as physiological saline, non-toxic buffers, preservatives and the like. For the purposes of the instant application, a pharmaceutically effective amount of the epigenetic modulating agent and binding molecule is an amount sufficient to affect the activity of at least one epigenetic modification in a cancer cell, e.g., to reduce histone deacetylase activity or DNA methyltransferase activity, and to achieve effective binding to a target and to achieve a benefit, e.g., an anti-proliferative effect, an inhibition, delay or reduction in tumor and malignant cell growth and metastases, the prevention of further tumor outgrowths, a reduction in tumor size, a decrease in tumor vasculature, and a reduction in the number of cancer cells, in a subject with cancer, and/or a decrease in one or more symptoms associated with the disease can be observed.

The pharmaceutical compositions used in the methods provided herein can include pharmaceutically acceptable carriers such as, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration can include sterile aqueous or non-aqueous solutions, suspensions, and emulsions. Non-limiting examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. Pharmaceutically acceptable carriers include, but are not limited to, 0.01-0.1 M, e.g., 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

Non-limiting examples of pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. Compositions are typically formulated to be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. Isotonic agents, for example, sugars, polyalcohols, such as mannitol, sorbitol, or sodium chloride can be included in the composition. Prolonged absorption of the injectable compositions can be brought about by including in the composition an agent which delays absorption, for example, aluminum monostearate and gelatin.

Sterile injectable solutions can be prepared by incorporating the active ingredients (e.g., an epigenetic modulating agent, e.g., an HDACi, a DNMTi, and/or a combination thereof in combination with an anti-SEMA4D antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, two non-limiting examples of methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture can have labels or package inserts indicating that the associated compositions are useful for treating a subject suffering from, or predisposed to cancer.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an epigenetic modulating agent, e.g., an HDACi, a DNMTi, and/or a combination thereof, and an anti-SEMA4D binding molecule, e.g., antibody, or fragment, variant, or derivative thereof, to be combined with the carrier materials to produce a single dosage form will vary depending upon the subject to be treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, the epigenetic modulating agent, e.g., the HDACi, the DNMTi, and/or a combination thereof in combination with the anti-SEMA4D binding molecule, e.g., the antibody, or antigen-binding fragment, variant, or derivative thereof can be administered to a human or other animal subject in accordance with the aforementioned methods of treatment in an amount sufficient to produce a therapeutic effect. The epigenetic modulating agent in combination with the anti-SEMA4D binding molecule, e.g., the antibody, or antigen-binding fragment, variant, or derivative thereof can be administered to such human or other animal in a conventional dosage form prepared by combining the antibody and epigenetic modulating agent with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising epigenetic modulating agent and binding molecule can be used.

By "effective amount" is intended an amount of the epigenetic modulating agent, e.g., the HDACi, the DNMTi, and/or a combination thereof, and an amount of the anti-SEMA4D binding molecule, e.g., the antibody, or antigen-binding fragment, variant, or derivative thereof, that when administered brings about a positive therapeutic response with respect to treatment of a patient with a disease to be treated, e.g., an anti-proliferative effect, the prevention of further tumor outgrowths, a reduction in tumor size, a decrease in tumor vasculature, a reduction in the number of cancer cells, the inhibition, delay, or reduction of tumor and/or malignant cell growth and/or metastases in a subject with cancer, and/or a decrease in one or more symptoms associated with the disease can be observed.

Therapeutically effective doses of the compositions described herein, e.g., for an anti-proliferative effect, the prevention of further tumor outgrowths, a reduction in tumor size, a decrease in tumor vasculature, a reduction in the number of cancer cells, the inhibition, delay, or reduction of tumor and/or malignant cell growth and/or metastases in a subject with cancer, and/or a decrease in one or more symptoms associated with the disease, can vary depending upon many different factors, including means of administration, target site, physiological state of the patient, whether the patient is human or other animal, other medications administered, and whether treatment is prophylactic or therapeutic. In certain embodiments the patient is a human, but non-human animals, including transgenic animals, can also be treated. Treatment dosages can be titrated using routine methods known to those of skill in the art to optimize safety and efficacy.

The amount the epigenetic modulating agent, e.g., the HDACi, the DNMTi, and/or a combination thereof in combination with the anti-SEMA4D binding molecule to be administered is readily determined by one of ordinary skill in the art without undue experimentation given the disclosure provided herein. Factors influencing the mode of administration and the respective amount epigenetic modulating agent and binding molecule include, but are not limited to, the severity of the disease, the history of the disease, and the age, height, weight, health, and physical condition of the individual undergoing therapy. Similarly, the amount of epigenetic modulating agent and binding molecule to be administered will be dependent upon the mode of administration and whether the subject will undergo a single dose or multiple doses of this agent.

The use of an epigenetic modulating agent, e.g., an HDACi, a DNMTi, and/or a combination thereof, in combination with an anti-SEMA4D binding molecule, e.g., antibody or fragment, variant, or derivative thereof, in the manufacture of a medicament for treating a subject with cancer, and in some aspects further including pretreatment with at least one other therapy, is also provided. By "pretreated" or "pretreatment" is intended the subject has received one or more other therapies (e.g., been treated with at least one other cancer therapy) prior to receiving the medicament comprising the epigenetic modulating agent in combination with the anti-SEMA4D binding molecule, e.g., antibody or antigen-binding fragment, variant, or derivative thereof "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the epigenetic modulating agent, e.g., HDACi, for example, Entinostat and/or DNMTi, for example, azacytidine, and an anti-SEMA4D binding molecule, for example, the monoclonal antibody VX15/2503 disclosed herein, or antigen-binding fragment, variant, or derivative thereof. It is not necessary that the subject was a responder to pretreatment with the prior therapy or therapies. Thus, the subject that receives the medicament comprising the epigenetic modulating agent in combination with an anti-SEMA4D binding molecule, e.g., an antibody or antigen-binding fragment, variant, or derivative thereof could have responded, or could have failed to respond, to pretreatment with the prior therapy, or to one or more of the prior therapies where pretreatment comprised multiple therapies.

The methods provided herein also provide for the use of an epigenetic modulating agent, e.g., an HDACi, a DNMTi, and/or a combination thereof, in combination with an anti-SEMA4D binding molecule, e.g., antibody, or antigen-binding fragment, variant, or derivative thereof, in the manufacture of a medicament for treating a subject with cancer, where the medicament is used in a subject that is also being treated with at least one other therapy. Available therapies disclosed herein include, without limitation, surgery, radiation therapy, a cancer vaccine, administration of an immunostimulatory agent, adoptive T cell or antibody therapy, administration of an immune checkpoint blockade inhibitor, administration of a regulatory T cell (Treg) modulator, or combination thereof.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein J., Immunology: The Science of Self-Nonself Discrimination (John Wiley & Sons, NY (1982)); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; W.H. Freeman and Co., NY); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Figure 1:
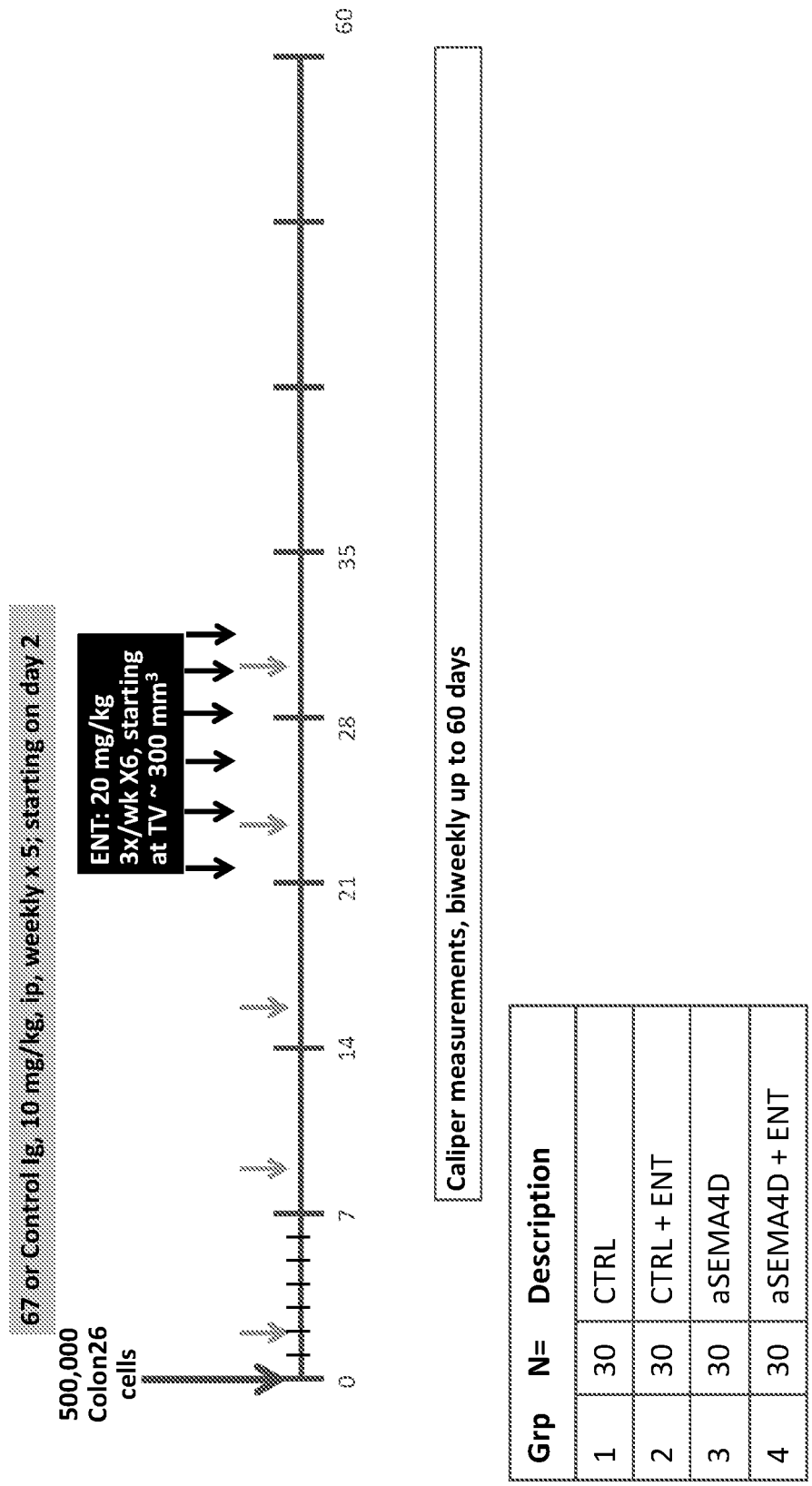
FIG. 1 shows the experimental design for combination therapy experiments in Examples 1 and 2.

Example 1: Administration of Entinostat (ENT) and Anti-SEMA4D Antibody Increases Survival, Significantly Delays Tumor Growth, and Increases Percent Complete Tumor Regression The effect of combined ENT and anti-SEMA4D MAb administration on survival, tumor growth, and tumor regression was tested in a tumor mouse model. Colon26 cells (500,000 cells) were implanted subcutaneously into Balb/c mice. Mice were treated with 1) control Ig (10 mg/kg, ip, weekly×5, starting on day 2) (n=20); 2) control Ig (10 mg/kg, ip, weekly×5, starting on day 2)+ENT (20 mg/kg, 3×/weekly×2 weeks, initiated when average tumor volume was ~300 mm$^3$) (n=21); 3) anti-SEMA4D/MAb 67 (10 mg/kg, IP, weekly×5 weeks, starting on day 2) (n=24); or 4) anti-SEMA4D/MAb 67 (10 mg/kg, IP, weekly×5 weeks, starting on day 2) and ENT (20 mg/kg, 3×/weekly×2 weeks, initiated when average tumor volume was ~300 mm$^3$)(n=26) (Experimental Design depicted in FIG. 1). Tumor volume at time of treatment was similar among control and experimental groups. Kaplan-Meier survival analysis was performed to assess survival function, change in tumor volume was measured to determine tumor growth rates, and frequency of complete tumor regression was evaluated by determining the percentage of tumor-free mice. Percent complete regression (% CR) was also stratified by tumors that exceeded at least 100 mm$^3$ before regressing. Statistical significance was determined using Mantel Cox Log Rank test for survival, 2-way ANOVA for tumor volume, and Fisher's exact test for CR. Prism reports results as non-significant (ns) at P>0.05, significant (symbolized by "*") at 0.01<P≤0.05, very significant ("") at 0.001<P≤0.01, extremely significant ("*") at P≤0.001, and highest significance ("****") at P≤0.0001. Mice that did not develop tumors or that developed tumor ulceration before reaching a tumor volume of 700 mm$^3$ were excluded from analysis.

A synergistic effect on tumor growth delay was seen for the combined ENT and anti-SEMA4D/MAb 67 administered group (782% maximal tumor growth delay (TGD)) compared to groups administered either agent alone: 107% TGD with SEMA4D/MAb 67 and 214% TGD with ENT (FIG. 2A). ENT and anti-SEMA4D/MAb 67 treated mice also exhibited a significant improvement in survival compared to mice treated with ENT or anti-SEMA4D/MAb 67 (p<0.05) (FIG. 2B). Furthermore, combined ENT and anti-SEMA4D/MAb 67 treatment significantly increased the frequency of complete tumor regression (62%***), especially among tumors that exceeded 100 mm$^3$ before regressing, compared to either single agent (FIGS. 2C and 2D). These results show that treatment with ENT and anti-SEMA4D MAb improved survival, reduced tumor growth, and resulted in regression of larger established tumors.

Example 2: Administration of ENT and Anti-SEMA4D Antibody Enhances Survival, Reduces Tumor Growth, and Increases Frequency of Complete Regression Colon26 cells (500,000 cells) were implanted subcutaneously into Balb/c mice. Mice were treated with 1) Control Ig (10 mg/kg, weekly×5 weeks, starting on day 2 (n=12)); 2) Control Ig (10 mg/kg, weekly×5 weeks, starting on day 2) and ENT (20 mg/kg, 3×/week×2 weeks, initiated when average tumor volume ~250 mm$^3$) (n=9); 3) anti-SEMA4D/MAb 67 (10 mg/kg, IP, weekly×5 weeks, starting on day 2) (n=8); or 4) anti-SEMA4D/MAb 67 (10 mg/kg, weekly×5 weeks, starting on day 2) and ENT (20 mg/kg, 3×/week×2 weeks, initiated when average tumor volume ~250 mm$^3$) (n=13). Tumor volume at the time of treatment was similar among control and experimental groups. Mean tumor volume, Kaplan Meier Survival curves, and frequency of complete tumor regression are shown for each group. Statistical significance was determined using 2-way ANOVA, Mantel Cox Log Rank test, and Fisher's exact test, respectively. Prism reports results as non-significant (ns) at P>0.05, significant (symbolized by "*") at 0.01<P≤0.05, very significant ("") at 0.001<P≤0.01, and extremely significant ("*") at P≤0.001. Mice that did not develop tumors or that developed tumor ulceration before reaching a tumor volume of 700 mm$^3$ were excluded from analysis.

The mice that received ENT and anti-SEMA4D/MAb 67 exhibited maximal 705% TGD, while mice treated with anti-SEMA4D/MAb67 showed a 119% delay in tumor growth (FIG. 3A). Combined treatment of mice with ENT and anti-SEMA4D/MAb 67 also increased the frequency of complete tumor regression (62%**), compared to Control Ig and ENT treatment groups (25%*) (FIGS. 3B-3D). Moreover, mice that received ENT and anti-SEMA4D/MAb 67 exhibited a significant improvement in survival compared to mice treated with Control Ig (P≤0.001) or Control Ig and ENT (p<0.01) (FIG. 3E). These results demonstrate that a combined treatment with ENT and anti-SEMA4D MAb resulted in enhanced survival, decreased tumor growth, and eradication or tumors.

Example 3: Administration of Azacytidine (AZA) and Anti-SEMA4D Antibody Increases Survival, Significantly Delays Tumor Growth, and Increases Percent Complete Tumor Regression The effect of combined AZA and anti-SEMA4D MAb administration on survival, tumor growth, and tumor regression was tested in a tumor mouse model. Colon26 cells (500,000 cells) were implanted subcutaneously into Balb/c mice. Mice were treated with: Group 1: control Ig (10 mg/kg, ip, weekly×4, starting on day 2 (n=12)); Group 2: anti-SEMA4D/MAb 67 (10 mg/kg, ip, weekly×4, starting on day 2 (N=8)); Group 3: control Ig (10 mg/kg, ip, weekly×4, starting on day 2+AZA (0.8 mg/kg, 3×/week×4 doses, starting on day 22-24, when average tumor volume is ~200 mm$^3$ (n=10)); and Group 4: anti-SEMA4D/MAb 67 (10 mg/kg, ip, weekly×4, starting on day 2+AZA (0.8 mg/kg, 3×/week×4 doses, starting on day 22-24, when average tumor volume is ~200 mm$^3$ (n=9)). The Experimental Design is depicted in FIG. 4). The mice were monitored for 60 days or until the tumor volumes reached about 1,500 mm$^3$.

Tumor volumes at time of treatment were similar among control and experimental groups. Kaplan-Meier survival analysis was performed to assess survival function, change in tumor volume was measured to determine tumor growth rates, and frequency of complete tumor regression was evaluated by determining the percentage of tumor-free mice. Statistical significance was determined using Mantel Cox Log Rank test for survival, 2-way ANOVA for tumor volume, and Fisher's exact test for complete tumor regression. Prism reports results as non-significant P>0.05, significant (symbolized by "*") at 0.01<P≤0.05, or very significant ("**") at 0.001<P≤0.01. Mice that did not develop tumors or that developed tumor ulceration before reaching a tumor volume of 700 mm$^3$ were excluded from analysis.

The mice that received AZA and anti-SEMA4D/MAb 67 exhibited maximal 705% TGD, while mice treated with anti-SEMA4D/MAb67 showed a 119% delay in tumor growth (FIG. 5A). AZA and anti-SEMA4D/MAb 67 treated mice also exhibited a significant improvement in survival compared to control mice (p<0.001) and nearly significant improvement in survival compared to single agent anti-SEDMA4D/MAb67 (p=0.0697) (FIG. 5B). Furthermore, combined AZA and anti-SEMA4D/MAb 67 treatment significantly increased the frequency of complete tumor regression to 78% (p<0.01), compared to Control Ig (17%) (FIG. 5C). These results show that treatment with AZA and anti-SEMA4D MAb improved survival, reduced tumor growth, and resulted in regression of larger established tumors.

The breadth and scope of the present disclosure should not be limited by any of the above-described exemplary embodiments, but should be defined only in accordance with the following claims and their equivalents.

TABLE 4

Sequences

| SEQ ID NO | Description | Sequence |
|---|---|---|
| 1 | VX15/2503 VH | QVQLVQSGAEVKKPGSSVKVSCKASGYSFSDYYMHW VRQAPGQGLEWMGQINPTTGGASYNQKFKGKATITV DKSTSTAYMELSSLRSEDTAVYYCARYYYGRHFDVW GQGTTVTVSS |
| 2 | VX15/2503 HCDR1 | GYSFSDYYMH |

TABLE 4-continued

Sequences

| SEQ ID NO | Description | Sequence |
|---|---|---|
| 3 | VX15/2503 HCDR2 | QINPTTGGASYNQKFKG |
| 4 | VX15/2503 HCDR3 | YYYGRHFDV |
| 5 | VX15/2503 VL | DIVMTQSPDSLAVSLGERATINCKASQSVDYDGDSYM NWYQQKPGQPPKLLIYAASNLESGVPDRFSGSGSGTD FTLTISSLQAEDVAVYYCQQSNEDPYTFGQGTKLEIK |
| 6 | VX15/2503 LCDR1 | KASQSVDYDGDSYMN |
| 7 | VX15/2503 LCDR2 | AASNLES |
| 8 | VX15/2503 LCDR3 | QQSNEDPYT |
| 9 | Mab 67 VH | QVQLQQSGPELVKPGASVKISCKASGYSFSDYYMHW VKQSPENSLEWIGQINPTTGGASYNQKFKGKATLTVD KSSSTAYMQLKSLTSEESAVYYCTRYYYGRHFDVWG QGTTVTVSS |
| 10 | Mab 67 VL | DIVMTQSPASLAVSLGQRATISCKASQSVDYDGDSYM NWYQQKPGQPPKLLIYAASNLESGIPARFSGSGSGTDF TLNIHPVEEEDAATYYCQQSNEDPYTFGGGTKLEIK |

What is claimed is:

1. A method for inhibiting, delaying, or reducing malignant cell growth in a subject with colon cancer, comprising administering to the subject a combination therapy comprising an effective amount of an isolated antibody or antigen-binding fragment thereof that specifically binds to semaphorin-4D (SEMA4D) and an effective amount of an epigenetic modulating agent selected from Entinostat (Pyridin-3-ylmethyl N-[[4-[(2-aminophenyl) carbamoyl] phenyl] methyl]carbamate), azacytidine and a combination thereof, wherein the antibody or fragment thereof comprises a variable heavy chain (VH) comprising VH CDRs 1-3 comprising SEQ ID NOS: 2, 3, and 4, respectively, and a variable light chain (VL) comprising VL CDRs 1-3 comprising SEQ ID NOS: 6, 7, and 8, respectively.

2. The method of claim 1, wherein the antibody or fragment thereof inhibits SEMA4D interaction with its receptor.

3. The method of claim 1, wherein the antibody or fragment thereof inhibits SEMA4D-mediated Plexin-B1 signal transduction.

4. The method of claim 1, wherein the VH and VL comprise, respectively, SEQ ID NO: 1 and SEQ ID NO: 5, or SEQ ID NO: 9 and SEQ ID NO: 10.

5. The method of claim 1, wherein the epigenetic modulating agent is Entinostat (Pyridin-3-ylmethyl N-[[4-[(2-aminophenyl)carbamoyl]phenyl]methyl]carbamate).

6. The method of claim 1, wherein the epigenetic modulating agent comprises azacytidine.

7. The method of claim 1, wherein:
the isolated antibody or antigen-binding fragment thereof that specifically binds to semaphorin-4D (SEMA4D) comprises a VH comprising the amino acid sequence SEQ ID NO: 1 and a VL comprising the amino acid sequence SEQ ID NO: 5, and
the epigenetic modulating agent comprises the HDACi Entinostat or the DNMTi azacytidine.

8. A pharmaceutical composition for the treatment of colon cancer comprising an effective amount of an isolated antibody or antigen-binding fragment thereof that specifically binds to semaphorin-4D (SEMA4D) and an effective amount of an epigenetic modulating agent selected from Entinostat (Pyridin-3-ylmethyl N-[[4-[(2-aminophenyl) carbamoyl] phenyl] methyl]carbamate), azacytidine and a combination thereof, wherein the antibody or fragment thereof comprises a variable heavy chain (VH) comprising VH CDRs 1-3 comprising SEQ ID NOS: 2, 3, and 4, respectively, and a variable light chain (VL) comprising VL CDRs 1-3 comprising SEQ ID NOS: 6, 7, and 8, respectively.

9. The pharmaceutical composition of claim 8, wherein the VH and VL comprise, respectively, SEQ ID NO: 1 and SEQ ID NO: 5, or SEQ ID NO: 9 and SEQ ID NO: 10.

10. The pharmaceutical composition of claim 8, wherein the epigenetic modulating agent is Entinostat (Pyridin-3-ylmethyl N-[[4-[(2-aminophenyl)carbamoyl]phenyl] methyl]carbamate).

11. The pharmaceutical composition of claim 8, wherein the epigenetic modulating agent is azacytidine.

12. A pharmaceutical composition for the treatment of colon cancer comprising:
an effective amount of an isolated antibody or antigen-binding fragment thereof that specifically binds to semaphorin-4D (SEMA4D), wherein the antibody or fragment thereof comprises the VH amino acid sequence SEQ ID NO: 1 and the VL amino acid sequence SEQ ID NO: 5, and
an effective amount of the HDACi Entinostat or an effective amount of the DNMTi azacytidine.

* * * * *

SEQUENCE LISTING

<160> NUMBER OF SEQ ID NOS: 10

<210> SEQ ID NO 1
<211> LENGTH: 118
<212> TYPE: PRT
<213> ORGANISM: Artificial Sequence
<220> FEATURE:
<223> OTHER INFORMATION: VX15/2503 VH

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
                20                  25                  30

Tyr Met His Trp Val Arg Gln Ala Pro Gly Gln Gly Leu Glu Trp Met
            35                  40                  45

Gly Gln Ile Asn Pro Thr Thr Gly Gly Ala Ser Tyr Asn Gln Lys Phe
        50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115
```

<210> SEQ ID NO 2
<211> LENGTH: 10
<212> TYPE: PRT
<213> ORGANISM: Artificial Sequence
<220> FEATURE:

```
<223> OTHER INFORMATION: VX15/2503 HCDR1

<400> SEQUENCE: 2

Gly Tyr Ser Phe Ser Asp Tyr Tyr Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: VX15/2503 HCDR2

<400> SEQUENCE: 3

Gln Ile Asn Pro Thr Thr Gly Gly Ala Ser Tyr Asn Gln Lys Phe Lys
1               5                   10                  15

Gly

<210> SEQ ID NO 4
<211> LENGTH: 9
<212> TYPE: PRT
<213> ORGANISM: Artificial Sequence
<220> FEATURE:
<223> OTHER INFORMATION: VX15/2503 HCDR3

<400> SEQUENCE: 4

Tyr Tyr Tyr Gly Arg His Phe Asp Val
1               5

<210> SEQ ID NO 5
<211> LENGTH: 111
<212> TYPE: PRT
<213> ORGANISM: Artificial Sequence
<220> FEATURE:
<223> OTHER INFORMATION: VX15/2503 VL

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 6
<211> LENGTH: 15
<212> TYPE: PRT
<213> ORGANISM: Artificial Sequence
<220> FEATURE:
<223> OTHER INFORMATION: VX15/2503 LCDR1

<400> SEQUENCE: 6

Lys Ala Ser Gln Ser Val Asp Tyr Asp Gly Asp Ser Tyr Met Asn
1               5                   10                  15
```

```
<210> SEQ ID NO 7
<211> LENGTH: 7
<212> TYPE: PRT
<213> ORGANISM: Artificial Sequence
<220> FEATURE:
<223> OTHER INFORMATION: VX15/2503 LCDR2

<400> SEQUENCE: 7

Ala Ala Ser Asn Leu Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: VX15/2503 LCDR3

<400> SEQUENCE: 8

Gln Gln Ser Asn Glu Asp Pro Tyr Thr
1               5

<210> SEQ ID NO 9
<211> LENGTH: 118
<212> TYPE: PRT
<213> ORGANISM: Artificial Sequence
<220> FEATURE:
<223> OTHER INFORMATION: Mab 67 VH

<400> SEQUENCE: 9

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
                20                  25                  30

Tyr Met His Trp Val Lys Gln Ser Pro Glu Asn Ser Leu Glu Trp Ile
            35                  40                  45

Gly Gln Ile Asn Pro Thr Thr Gly Gly Ala Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: Mab 67 VL

<400> SEQUENCE: 10

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45
```

```
Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```